US006455282B1

(12) United States Patent
Beck et al.

(10) Patent No.: US 6,455,282 B1
(45) Date of Patent: *Sep. 24, 2002

(54) CELLS, VECTORS AND METHODS FOR PRODUCING BIOLOGICALLY ACTIVE TSH

(75) Inventors: Anton Beck, Wellsley; Edward Bernstine, Boston; Nancy Hsiung, Wellesley; Vermuni B. Reddy, Framingham, all of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/970,227

(22) Filed: Nov. 2, 1992

Related U.S. Application Data

(63) Continuation of application No. 07/318,536, filed on Jul. 18, 1989, now abandoned, which is a continuation of application No. 07/016,673, filed on Feb. 19, 1987, now abandoned, which is a continuation-in-part of application No. 06/811,959, filed on Dec. 20, 1985, now abandoned, which is a continuation of application No. 06/548,211, filed on Nov. 2, 1983, now abandoned.

(51) Int. Cl.$^7$ .......................... C12N 15/09; C12N 5/00; C12N 15/63

(52) U.S. Cl. .................. 435/69.4; 435/70.1; 435/320.1; 435/325; 435/455

(58) Field of Search ............................ 435/69.4, 320.1, 435/240.2, 69.1, 172.3, 70.1, 325, 455; 536/23.5, 23.1, 23.51, 24.1; 935/6, 9, 13, 27, 32; 530/399

(56) References Cited

U.S. PATENT DOCUMENTS

| | | | |
|---|---|---|---|
| 4,383,034 A | | 5/1983 | Sugimoto |
| 4,419,446 A | | 12/1983 | Howley et al. |
| 4,468,464 A | * | 8/1984 | Cohen et al. |
| 4,656,134 A | | 4/1987 | Ringold ........................ 435/91 |
| 4,840,896 A | | 6/1989 | Reddy et al. |
| 4,923,805 A | | 5/1990 | Reddy et al. .............. 435/69.4 |
| 5,156,957 A | * | 10/1992 | Reddy et al. |
| 5,240,832 A | * | 8/1993 | Kelton et al. |
| 5,639,639 A | | 6/1997 | Reddy et al. |
| 5,639,640 A | | 6/1997 | Reddy et al. |
| 5,767,251 A | | 6/1998 | Reddy et al. |
| 5,856,137 A | | 1/1999 | Reddy et al. |

FOREIGN PATENT DOCUMENTS

GB 2137631 10/1984

OTHER PUBLICATIONS

Vamuakopoulos Et Al (1980) Proced. Natl. Acad. Sci. 77, 3149–3153.*
Liu Et Al (1982) DNA 1, 213–221.*
Hamer Et Al (1982) J. Molec. Appl. Genet. 1, 273–288.*
DiMaio Et Al (1982) Proced. Natl. Acad. Sci. 79, 4030–4034.*
Chemical Abstracts, vol. 108, No. 3 Issued 1987, Jan. 18 (Columbus Ohio, USA), Stewart, F. "Application of Recombinant DNA Techniques to Structure–Functions Studies of Equine Protein Hormones" See p. 147, col. 1–2, Abstract No. 17058w, J. Reprod. Fertil. Suppl. (1987) 35: 1–8.
Chemical Abstracts, vol. 107, No. 17 Issued 1987, Oct. 26 (Columbus Ohio, USA), Nilson, J. "Expression of the Genes Encoding Bovine LH in a Line of Chinese Hamster Ovary Cells" See p. 187, col. 2, Abstract No. 148529C, J. Reprod. Fertil. Suppl. (1987) 34: 227–36.
Chemical Abstracts, vol. 106, No. 17, Issued 1987, Apr. 27 (Columbus Ohio USA) Schwartzbouer, J "Efficient and Stable Expression of Recombinant Fibronectin Polypeptides" See P. 173, col. 1, Abstract No. 132796f Proc. Natl Acad Sci USA (1987) 84: 754–8.
Chemical Abstracts, vol. 103, No. 7, Issued 1985, Aug. 19 (Columbus, Ohio USA) Reddy, V. "Heterodimeric Human Fertility Hormones" See p. 146, col. 1, Abstract No. 49165d, PCT WO 85 01958, May 9, 1985.
Chemical Abstracts, vol. 103, No. 9, Issued 1985, Sep. 2 (Columbus, Ohio USA) Reddy, V. Heterodimeric Human Fertility Hormones, See p. 182, col. 1–2, Abstract No. 66081d, PCT WO 85 01959, May 9, 1985.
Kaetzel, D. Et Al. (May 5, 1988) J.Biol. Chem. vol. 263: 6344–6351 Methotrexate–Induced Amplification of the Bovine Lutropin Genes in Chinese Hamster Ovary Cells. Relative Concentration of the Alpha and Beta Subunits Determines the Extent of Heterodimer Assembly.
Kaetzel, D. Et Al. (Nov. 1985) Proc. Natl. Acad. Sci. USA, vol. 82: 7280–7283 Expression of Biologically Active Bovine Luteinizing Hormone in Chinese Hamster Ovary Cells.
Chemical Abstracts, vol. 109, No. 7 Issued 1988, Aug. 14 (Columbus Ohio, USA), Kato, Y. "Cloning and DNA Sequence Analysis of the cDNA for the Precursor of Porcine Follicle Stimulating Hormone Beta Subunit" See p. 182, col. 2, Abstract No. 49432a, Mol. Cell. Endocrinol (1988) 55: 107–12.
Cole Et Al (1993) Bio/Technology 11, 1014–1024.*
Rathnam et al., "Primary Aminbo Acid Sequence of Follicle–stimulating Hormone from Human Pituitary Glands", *The Journal of Biological Chemistry* 250(17):6735–6746 (1975).

(List continued on next page.)

Primary Examiner—Deborah Crouch
(74) Attorney, Agent, or Firm—Browdy and Neimark, P.L.L.C.

(57) ABSTRACT

Biologically active heteropolymeric protein composed of a plurality of subunits, both subunits being synthesized in a single cell having an expression vector comprising heterologous DNA encoding the subunits. Preferably the protein is similar to the human or ungulate fertility hormones, LH and FSH.

17 Claims, 27 Drawing Sheets

OTHER PUBLICATIONS

Saxena et al., "Amino Acid Sequence of the Beta Subunit of Follicle–stimulating Hormone from Human Pituitary Glands", *The Journal of Biological Chemistry* 251(4):993–1005 (1976).

Pierce et al., "Glycoprotein Hormones: Structure and Function", *Ann Rev. Bioch.* 50:465–496 (1981).

Fiddes et al., "The cDNA for the beta–subunit of human chorionic gonadotropin suggests evolution of a gene by readthrough into the 3'–untranslated region", *Nature* 286:684–687 (1980).

Chappel, S. et al., "Biosynthesis and Secretion of Follicle–Stimulating Hormone", *Endocrine Reviews* 4(2):179–211 (1983).

Fiddes et al., "The Gene Encoding the Common Alpha Subunit of the Four Human Glycoprotein Hormones", *J. Mol. Appl. Gene* 1:3–18 (1981).

Elder, J.T. et al., *Ann. Rev. Genet.* 15:328–330 (1981).

Rice, D. et al., "Regulated expression of an immunoglobulin in K gene introduced into a mouse lymphoid cell line", *Proc. Natl. Acad. Sci.* 79:7862–7865 (1982).

Moriarty, A. et al., "Expression of the hepatitis B virus surface antigen gene in cell culture by using a simian virus 40 vector", *Proc. Natl. Acad. Sci.* 78:2606–2610 (1981).

Lusthader, J. et al., "Characterization of the HCG alpha subunit expressed by a recombinant DNA vector in mouse C127 cells", 68th Annual Meeting of the Endocrine Society, Abstract #513.

Ochi, A. et al., "Functional Immunoglobulin M Production After Transfection of Cloned Immunoglobulin in Heavy and Light Chain Into Lymnphoid Cells," *Proc. Acad. Sci. USA* 80:6351–6355 (1983).

\* cited by examiner

FIG. 11
Bovine α Subunit cDNA

```
  1 GCAGTTGCTG AGAAATCACA AGACAAAACT AAAATTCTTC TTCAGATCCA
 51 CAGTCAACTG CCCTGACTAC ATTCTGCAAA AATCCAGAGG ACGAAGAGCC
101 ATGGATTACT ACAGAAAATA TGCAGCTGTC ATTCTGGCCA TTTTGTCTCT
151 GTTTCTGCAA ATTCTCCATT CCTTTCCTGA TGGAGAGTTT ACAATGCAGG
201 GCTGTCCTGA ATGCAAGCTA AAGAAAACA AATACTTCTC CAAGCCAGAT
251 GCTCCAATCT ATCAGTGCAT GGGGTGCTGC TTCTCCAGGG CATACCCCAC
301 TCCAGCGAGG TCTAAGAAGA CAATGTTGGT CCCCAAGAAC ATCACCTCGG
351 AAGCTACATG CTGTGTGGCC AAAGCATTTA CCAAGGCCAC AGTGATGGGA
401 AATGTCAGAG TGGAGAACCA CACCGAGTGC CACTGCAGCA CTTGTTATTA
451 TCACAAATCC TAATAGTTTG CAGTGGGCCT TGCTGATGAT GGCTGACTTG
501 CTCAAAAGGA AAATTAATTT GTCCAGTGTC TATGGCTTTG TGAGATAAAA
551 CCCTCCTTTT CCTTGCCATA CCATTTTTAA CCTGCTTTGA GAATATACTG
601 CAGCTTTATT GCTTTCTCC TTATCCTACA ATATAATCAG TAGTCTTGAT
651 CTTTTCATTT GGAATGAAAT ATGGCATTTA GCATGACCAT AAAAAGCTGA
701 TTCCACTGGA AATAAAGTCT TTTAAATCAT C
```

FIG. 12
Bovine β LH

```
  1  CGATGTTCCA GGGACTGCTG CTGTGGCTGC TGCTGGGCGT GGCCGGGGTG
 51  TGGGCTTCCA GGGGGCCACT GCGGCCGCTG TGCCAGCCCA TCAACGCCAC
101  CCTGGCGGCT GAGAAGGAGG CCTGCCCTGT CTGTATCACT TTCACCACCA
151  GCATCTGCGC CGGCTACTGC CCCAGCATGA AGCGGGTGCT GCCTGTCATC
201  CTGCCGCCCA TGCCCCAGCG GGTGTGCACC TACCATGAGC TGCGCTTCGC
251  CTCCGTTCGG CTCCCCGGCT GCCCACCTGG AGTGGACCCA ATGGTCTCCT
301  .TCCCCGTGGC CCTCAGCTGT CACTGTGGAC CCTGCCGCCT CAGCAGCACT
351  GACTGCGGGG GTCCCAGAAC CCAACCCTTG GCCTGTGACC ACCCCCCGCT
401  .CCCAGACATC CTCTTCCTCT AAGGATGCCC CACTTCAACC TCCCATGCCC
451  ATCCTAACTC TGGAAACCAG CAGACACTCT TCCCCTCCCT TCCCAATAAA
501  GACTTCTCAA ACTGCAAAAA AAAAA
```

FIG. 13
Bovine β FSH

```
  1  GGATCCGTCA GCATCTACAG TTATCAAGTG CCCAGGATGA AGTCTGTCCA
 51  GTTCTGTTTC CTTTTCTGTT GCTGGAGAGC AATCTGCTGC AGAAGCTGCG
101  AGCTGACCAA CATCACCATC ACGGTGGAGA AAGAGGAATG TGGCTTCTGC
151  .ATAAGCATCA ACACCACGTG GTGTGCAGGC TACTGCTACA CCCGGGACTT
201  GGTGTACAGG GACCCAGCAA GGCCCAATAT CCAGAAAACG TGTACCTTCA
251  AGGAGCTGGT CTACGAGACG GTGAAAGTGC CTGGCTGTGC TCACCATGCA
301  GACTCCCTGT ACACGTACCC AGTAGCCACT GAATGTCACT GCAGCAAGTG
351  CGACAGCGAC AGCACTGACT GCACCGTGCG AGGCCTGGGG CCCAGCTACT
401  GCTCCTTCAG GGAAATCAAA GAATAAAGAG CAGCGGATGC TTTGAGCTGC
451  CTACCCTTAT CCTAAAGGAC CAAAACATCC AAGATGTCTG TGTGTACATG
501  TGCGTAGGCT GCAGACCACC ACGGGAGACC CTACTGACCT CTGCTCTCCT
551  GACGGATCC
```

FIG. 18 Porcine α Subunit

```
  1 CTGCAGGGGG GGGGGGGGCG CAACCCAAGC TAATATCCCT CTTCAGGTCC
 51 ACAATCAACT GCCCTTGAAC ACATCCTGCA AAAAATCCAG AGGAAGAAGA
101 GCCATGGATT ACTACAGAAA ATATGCAGCT GTCATCCTGG CCATATTGTC
151 TGTGTTTCTG CAAATTCTCC ATTCCTTTCC TGATGGAGAG TTTACAATGC
201 AGGGCTGCCC AGAATGCAAG CTAAAGGAAA CAAGTACTT CTCCAAGCTG
251 GGTGCCCCAA TCTATCAGTG CATGGGCTGC TGCTTCTCCA GAGCGTACCC
301 AACTCCAGCG AGGTCCAAGA AGACAATGTT GGTTCCAAAG AACATCACCT
351 CGGAAGCCAC ATGCTGTGTG CCAAAGCAT TTACCAAGGC ACACAGTAATG
401 GGAAATGCCA GAGTGGAGAA CCACACCGAA TGCCACTGCA GTACTTGTTA
451 TTATCACAAA TCTTAAATAT TTTGCAGAGG GCCTTGTTGA TGACTGCTGA
501 TTTCTCAGAA TGAAAAATTA ATTTGTTCAG TGTCTATGGC TTTGGGAGAT
551 AAAATCCTCG CTTTTCTTTA CCATACCATC TTTTACACGC TTTAAGAATG
601 TGCTGCAG
```

FIG. 20
pFSHβ

```
  1 GAGTGGCTAC CTGGATACGT ATACAGGGAG TCTGCATGGT GAGCACAGCC
 51 AAGTACTTTC ACGGTCTCGT ACACCAGCTC CTTAATTGTT TGGTTTCCAC
101 CCCAAGATGA AGTCGCTGCA GTTTTGCTTC CTATTCTGTT GCTGGAAAGC
151 CATCTGCTGC AATAGCTGTG AGCTGACCAA CATCACCATC ACAGTGGAGA
201 AGAGGAGTG TAACTTCTGC ATAAGCATCA ACACCACGTG GTGTGCTGGC
251 TATTGCTACA CCCGGGACCT GGTATACAAG GACCCAGCCA GGCCCAACAT
301 CCAGAAAACA TGTACCTTCA AGGAGCTGGT GTACGAGACC GTGAAAGTAC
351 CTGGCTGTGC TCACCATGCA GACTCCCTGT ATACGTATCC AGTAGCCACC
401 GAATGTCACT GTGGCAAGTG TGACAGTGAC AGTACTGACT GCACCGTGAG
451 AGGCCTGGGG CCCAGCTACT GCTCCTTCAG TGAAATGAAA GAATAAAGAG
501 CAGTGGACAT TTCATGCTTC CTACCCTTGT CTGAAGGACC AAGACGTCCA
551 AGAAGTTTGT GTGTACATGT GCCCAGGCTG CAAACCACTA TGAGAGACCC
601 CACTGATCCC TGCTGTCCTG TGGAGGAGGA GCTCCAGGAA TGCAGAGTGC
651 TAGGGCCTCA GTCCCATCAC CACTCAACCC TGTATTTTGG GTCTGGTTCC
701 ATAAGTTTTA TTCGGTCTTT TTTTTTTAAA TTACTCAATG AATTTTATTA
751 CATTTATAAT TGTAGCAAGG ATCATCACAA
```

FIG. 21
eLHβ

```
  1 GGGGGGGGGG GGGGGGGGGG GGGTTAAATT TGTAAGACCA GAGTAAACAC
 51 GGCAGAGGAG GCACCGAGGA TGGAGACGCT CCAGGGGCTG CTGCTGTGGA
101 TGCTGCTGAG TGTTGGCGGG GTCTGGGCAT CCAGGGGGCC ACTGCGGCCA
151 CTGTGCCGGC CCATCAACGC CACTCTGGCT GCTGAGAAGG AGGCCTGCCC
201 CATCTGCATC ACCTTCACCA CCAGCATCTG TGCCGGCTAC TGCCCCAGCA
251 TGGTGCGGGT GATGCCAGCT GCCCTGCCGG CCATTCCCCA GCCAGTGTGC
301 ACCTACCGTG AGCTGCGCTT TGCTTCCATC CGGCTCCCCG GCTGCCCGCC
351 TGGTGTGGAC CCCATGGTCT CCTTCCCCGT GGCCCTCAGT TGTCACTGCG
401 GGCCCTGCCA GATCAAGACC ACTGACTGCG GGGTTTTCAG AGACCAGCCC
451 TTGGCCTGTG CCCCCAGGC CTCCTCTTCC TCTAAGGATC CCCCATCCCA
501 ACCTCTCACA TCCACATCCA CCCCAACTCC TGGGGCCAGC AGACGTTCCT
551 CTCATCCCCT CCCAATAAAG ACTTCTTGAA CTACAAAAAA AAAAAAAAAA
601 AAAAAAAAA A
```

FIG. 23
Equine α Subunit

```
  1 GGGGGGGGGG GGGGGGGGGG CTGCTCTGAA CACATCCTAC AAAAAGTCCA
 51 GAGGAAGAAG AGCCATGGAT TACTACAGAA ACATGCAGC TGTCATCCTG
101 GCCACATTGT CCGTGTTTCT GCATATTCTC CATTCCTTTC CTGATGGAGA
151 GTTTACAACG CAGGATTGCC CAGAATGCAA GCTAAGGGAA AACAAGTACT
201 TCTTCAAACT GGGCGTCCCG ATTACCAGT GTAAGGGCTG CTGCTTCTCC
251 AGAGCGTACC CCACTCCAGC AAGGTCCAGG AAGACAATGT TGGTCCCAAA
301 GAACATCACC TCAGAATCCA CATGCTGTGT GGCCAAAGCA TTTATCAGGG
351 TCACAGTGAT GGGAAACATC AAGTTGGAGA ACCACACCCA GTGCTATTGC
401 AGCACTTGCT ATCACCACAA GATTAAATG TTTCACCAAG TGCCTTGTGG
451 ATGACTGCTG ATTCCACCC CCCCCCCCC
```

FIG. 27
Equine β FSH

```
  1  TTTTGTTTGG TCAGCTTATA CAATGATCGT AAGTCTTTGG TTTTCGGTTT
 51  CTCATAGGCC TTAATTGTTC GTTCCAGCCC AAGATGAAGT CAGTCCAGTT
101  TTGTTTCCTT TTCTGTTGCT GGAAAGCAGT CTGCTGCAAT AGCTGTGAGC
151  TGACCAACAT CACCATCGCC GTGGAGAAGG AGGAATGTGG CTTCTGCATA
201  AGCATCAACA CCACCTGGTG TGCGGGCTAC TGCTACACCC GGGACCTGGT
251  GTACAAGGAC CCAGCCCGGC CAACATCCA GAAAACATGC ACCTTCAAGG
301  AGCTGGTGTA CGAGACAGTC AAAGTGCCTA GCTGTGCTCA CCACGCGGAC
351  TCCCTGTACA CGTACCCGGT GGCCACTGCA TGTCACTGTG GCAAATGTAA
401  CAGCGACAGC ACTGACTGCA CCGTGCGAGG TCTGGGGCCC AGCTACTGCT
451  CCTTCGGTGA CATGAAGGAA TAAAGAACGC TGACATTGTG GCTGCCTGCC
501  CTTGCCTGAA GGACCAAGAT ACCCAAAATG TCTGTGTGTG TCCCATGTGC
551  TCAGGTTGCA AACAGCTGTG GGAGACCCTG CTGACCTCTG CTCTCCTGGC
601  AGAGCGGGAG CTGCAG
```

FIG. 32
pLHβ

```
  1  GGGGGGGGGG GGGGGGGGGG GGGGGGGGCC AGGGACTGCT GTTGTGGCTG
 51  CTGCTGAGCG TGGCCGGGGT GTGGGCATCC AGGGGCCAC TGCGGCCTCT
101  GTGCCGGCCC ATCAACGCCA CCCTGGCTGC TGAGAATGAG GCTTGCCCTG
151  TCTGCATCAC CTTCACCACC AGCATCTGTG CCGGCTACTG TCCAGCATG
201  GTGCGGGTGC TGCCGGCTGC CCTGCCACCC GTGCCCCAGC CGGTGTGCAC
251  CTACCGAGAG CTGAGCTTTG CCTCCATCCG CCTCCCTCCC TGCCCGCCTG
301  GCGTGGACCC AACGGTCTCC TTCCCCGTGG CTCTCAGCTG TCACTGCGGG
351  CCCTGCCGCC TCAGCAGCTC TGACTGTGGG GGTCCCAGAG CCCAACCCTT
401  GGCCTGTGAC CGCCCCTAC TCCCAGGCCT CCTCTTCCTC TAAGGACTCC
451  CGGCCTCAGC CTCCCAGGCC CACAGATGCT CCCCCCCACC AATAAAGGCT
501  GCTCCACCTG CAAACCCCCC CCCCCCCCCC CCCCCCCCCC
```

CELLS, VECTORS AND METHODS FOR PRODUCING BIOLOGICALLY ACTIVE TSH

This application is a continuation of Ser. No. 07/318,536, filed Jul. 18, 1989, now abandoned, which is a continuation of Ser. No. 07/016,673, filed Feb. 19, 1987, now abandoned, which is a CIP of Ser. No. 06/811,959, filed Dec. 20, 1985, now abandoned, which is a continuation of Ser. No. 06/548,211, filed Nov. 3, 1983, now abandoned.

BACKGROUND OF THE INVENTION

This invention relates to the use of recombinant DNA techniques to produce heteropolymeric proteins.

Various polypeptide chains have been expressed, via recombinant DNA technology, in host cells such as bacteria, yeast, and cultured mammalian cells. Fiddes et al., Nature 281:351, 1979, and Fiddes et al., Nature 286:684, 1980, describe the cloning of, respectively, the $\alpha$ and $\beta$ subunits of human choriogonadotropin (hCG).

Kaname U.S. Pat. No. 4,383,036 describes a process for producing hCG in which human lymphoblastoid cells are implanted into a laboratory animal, harvested from the animal, and cultured in vitro; accumulated hCG is then harvested from the culture.

SUMMARY OF THE INVENTION

In general, the invention features, in one aspect, a biologically active heteropolymeric protein composed of a plurality of subunits, both subunits being synthesized in a single cell having an expression vector containing heterologous DNA encoding the subunits. In related aspects the vector is autonomously replicating (i.e., not integrated into the chromosome of the host cell).

In preferred embodiments, the protein is synthesized by a eukaryotic cell, and the protein is modified post-translationally, most preferably by glycosylation; and the protein is a secreted protein such as a hormone, most preferably a fertility hormone such as hCG, luteinizing hormone (LH) or follicle stimulating hormone (FSH); or the hormone thyroid stimulating hormone (TSH). In other preferred embodiments the protein is an ungulate fertility hormone selected from LH and FSH; the ungulate being chosen from a horse, pig or cow.

In another aspect, the invention features a cell, containing a first expression vector, which cell is capable of producing a biologically active heteropolymeric protein that is encoded at least in part by the vector. In preferred embodiments, a second expression vector (which may be autonomously replicating) encodes a second portion of the protein or at least two subunits of the protein are encoded by a single expression vector; the protein is hCG or human luteinizing hormone (LH), or an ungulate fertility hormone selected from LH and FSH; the vector is a replicating virus or a plasmid; the cell is a monkey or mouse cell; transcription of the different subunits is under the control of the SV40 late promoter; transcription of the $\alpha$ subunit of the protein is under the control of the SV40 early promoter and transcription of the $\beta$ subunit is under control of the mouse metallothionein promoter, or transcription of both subunits is under the control of the mouse metallothionein promoter; and the expression vector which includes the mouse metallothionein promoter also includes at least the 69% transforming region of the bovine papilloma virus (BPV) genome.

In another aspect, the invention features an expression vector (which may be autonomously replicating) including two genes encoding two different heterologous proteins, the genes being under the control of two different promoters, most preferably a metallothionein promoter and a BPV promoter; the use of different promoters advantageously minimizes the possiblity of deleterious recombinations.

In preferred embodiments of the above aspects the vector comprises at least a part of a DNA sequence chosen from the DNA sequences shown in FIG. 11, 12, 13, 18, 20, 21, 23, 27 or 32; and the fragment in the vector is chosen from those fragments deposited in cells in the N.R.R.L. with accession number B18124, B18125, B18126, B18127, B18128, B18139, B18140, B18131, or B15793.

As used herein, "subunit" refers to a portion of a protein, which portion, or homologue or analogue thereof, is encoded in nature by a distinct mRNA. Thus, for example, a heavy chain and a light chain of an IgG immunoglobulin are each considered a subunit. Insulin, on the other hand, is composed of two chains which are not considered subunits, because both are, in nature, encoded by a single mRNA, and cleavage into two chains naturally occurs only after translation.

The term "expression vector" refers to a vector which includes heterologous (to the vector) DNA under the control of control sequences which permit expression in a host cell. Such vectors include replicating viruses, plasmids, and phages. The term "heterologous DNA" is used to refer to DNA which does not naturally occur adjacent to any other DNA which is also being referred to.

The invention permits the production of a biologically active heteropolymeric protein from a single culture of transformed cells. We have found that when the $\alpha$ subunits of a heteropolymeric protein are produced alone they are modified by the host cell. This modification prevents recombination of the $\alpha$-subunit with the $\beta$-subunit. Thus, biosynthesis of an active gonadotropin (i.e., $\alpha$-and-$\beta$-subunits linked by ionic bonds) cannot occur in genetically engineered cells unless a system is used to produce both within a single cell so that combination of the subunits occurs prior to post-translational modification. This invention describes and provides the technology required for the establishment of stable cell lines transfected with foreign DNA that encodes for the biosynthesis of balanced amounts of both $\alpha$ and $\beta$-subunits. These cell lines allow expression of biologically active dimeric glycoprotein hormones. The system allows production of proteins, in a single culture, which undergo, in the culture, post-translational modification, e.g. glycosylation and proteolytic processing, for activity or stability.

The use of autonomously replicating expression vectors prevents undesirable influence on the desired coding regions by control sequences in the host chromosome.

Other advantages and features of the invention will be apparent from the following description of the preferred embodiments thereof, and from the claims.

DESCRIPTION OF THE PREFERRED EMBODIMENTS

We turn now to the preferred embodiments of the invention, first briefly describing the drawings thereof.

DRAWINGS

FIG. 11 is a part of the DNA sequence from a bovine β clone.

FIG. 12 is a part of the DNA sequence from a bovine βLH clone.

FIG. 13 is a part of the DNA sequence from a bovine βFSH clone.

FIG. 18 is a part of the DNA sequence from the porcine α clone.

FIG. 20 is a part of the DNA sequence from the porcine βFSH clone.

FIG. 21 is a part of the DNA sequence from the equine βLH clone.

FIG. 23 is a part of the DNA sequence of the equine α clone.

FIG. 27 is a part of the DNA sequence from the equine βFSH clone.

FIG. 32 is a part of the DNA sequence of a cDNA clone of porcine βLH.

STRUCTURE

Figure 1:
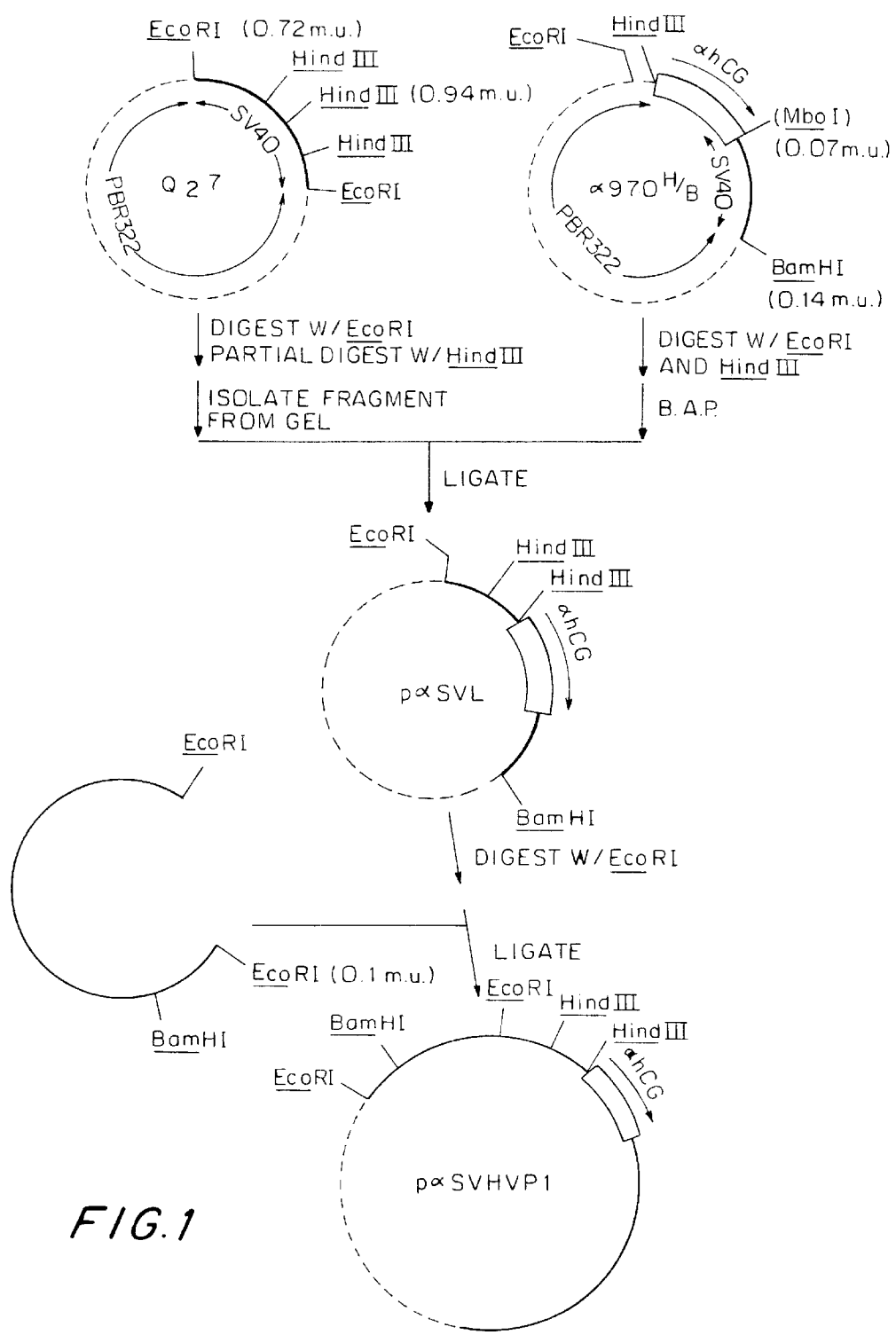
FIG. 1 is a diagrammatic illustration of the construction of the plasmid p$\alpha$ SVHVPl, which contains the $\alpha$ hCG cDNA clone, portions of SV40 viral DNA, and sequences of the plasmid pBR322.

The cloning vectors of the invention have the general structure recited in the Summary of the Invention, above. Preferred vectors have the structures shown in the Figures, and are described in more detail below. In each example the vectors were used to express the α and β subunits of each of various hormones encoded by human, or ungulate DNAs. Three ungulate examples are presented: horse, cow and pig. It is understood that these examples are not limiting to the invention; those skilled in the art can use the methods described to isolate and express equivalent genes from other animals and ungulates.

Each example describes the methods used to isolate the appropriate RNA, prepare a cDNA bank and then identify the desired clones.

Most of the techniques used herein are described in detail in Maniatis et al. (1982) Molecular Cloning: A Laboratory Manual (Cold Spring Harbor Laboratory), hereby incorporated by reference.

HUMAN HORMONES

EXAMPLE 1

Human CG (hCG)

RNA is extracted from human placental tissue by the following method. Homogenization of the tissue is carried out in a 1:1 mixture of phenol:100 mM Na-acetate (pH 5.5) containing 1 mM EDTA, that has been warmed to 60° C. for 20 min. After cooling on ice for 10 min., the phases are separated by centrifugation. The hot phenol extraction is repeated twice more followed by two extractions with chloroform.

RNA is precipitated from the final aqueous phase by the addition of 2.5 volumes of ethanol.

In order to enrich for poly A+ mRNA, placental RNA is passed over oligo (dT)-cellulose in 0.5M NaCl buffered with 10 mM Tris-HCl, pH 7.5, and washed with the same solution. Poly A+ mRNA is eluted with 10 mM Tris-HCl (pH 7.5), 1 mM EDTA, 0.05% SDS and precipitated twice with ethanol. Typical initial yields are 1.5–2.0 mg of total RNA per g of tissue, of which about 2% is poly A+ mRNA.

Placental cDNA libraries are constructed by reverse transcription of placental mRNA, second strand synthesis using *E. coli* DNA polymerase I (large fragment), treatment with SI nuclease, and homopolymer tailing (dC) with terminal deoxynucleotidyl transferase; all such procedures are by conventional techniques.

In a typical preparation, 20–30% conversion of mRNA to single strand (ss) cDNA; 70% resistance to digestion with nuclease S1 after second strand synthesis; and dC "tails" of ten to twenty-five bases in length, are obtained. These cDNA molecules are then annealed to DNA fragments of the plasmid pBR 322, which has been digested with PstI, and to which dG "tails" have been added. These recombinant plasmids are then used to transform *E. coli* cells to generate a cDNA library (transformed cells are selected on the basis of tetracycline resistance).

In order to identify the human α hCG clone, a 219 bp AluI fragment of a mouse α thyroid stimulating hormone (TSH, Chin et al., Proc. Nat. Acad. Sci., 78:5329, 1981) clone is used as a hybridization probe. This probe has 77% sequence homology with the human clone. It is radioactively labeled by nick translation and hybridized to the cDNA library under conditions that take into account the extent of homology. Strongly hybridizing clones are analyzed by restriction mapping and clones containing the complete coding sequence of α hCG are verified by DNA sequencing.

Construction of Plasmid p α SVHVPl

Referring to FIG. 1, in order to construct the plasmid α 970 H/B one of the above-described cDNA clones, containing the α hCG fragment, is digested with NcoI. The NcoI site, just 5' to the ATG codon signalling initiation of translation, is filled in and ligated to a synthetic HindIII linker. Similarly, the natural HindIII site in the 3' untranslated region of the clone is cut, filled in with E. coli DNA polymerase Klenow, and then ligated to a synthetic BamHI linker. This fragment is cloned into the plasmid pBR322 between its HindIII and BamHI sites to generate the plasmid α 574 H/B. This plasmid is digested with BamHI, treated with alkaline phosphatase, and ligated to the 396 bp Sau3A fragment of SV40 DNA (from 0.07 to 0.14 map units, m.u.) which has been isolated from a polyacrylamide gel. The ligation mix is used to transform E. coli to ampicillin resistance and the desired plasmid, α 970 H/B, is identified among the transformants.

The plasmid $Q_2 7$ is constructed by cutting SV40 at its HpaII site, making flush ends by digestion with nuclease S1, ligating on EcoRI linkers, digesting with EcoRI, and cloning the resulting 1436 bp fragment into the EcoRI site of pBR322.

Referring to FIG. 1, $Q_2 7$ is digested completely with EcoRI and partially with HindIII; the fragment from 0.72 to 0.94 map units is isolated and cloned into α 970 H/B, which has been digested with EcoRI and HindIII and treated with alkaline phosphatase. The ligation mix is used to transform E. coli, and the desired plasmid, p α SVL, is identified among the transformants by restriction mapping.

p α SVL is digested with EcoRI and the fragment of SV40, with EcoRI ends, extending from 0 to 0.72 map units, and containing the SV40 origin of replication and the intact early region, is ligated to it to generate the plasmid p α SVHVPl, which is isolated from E. coli transformants.

Construction of Plasmid p β SVVPl

Figure 2:
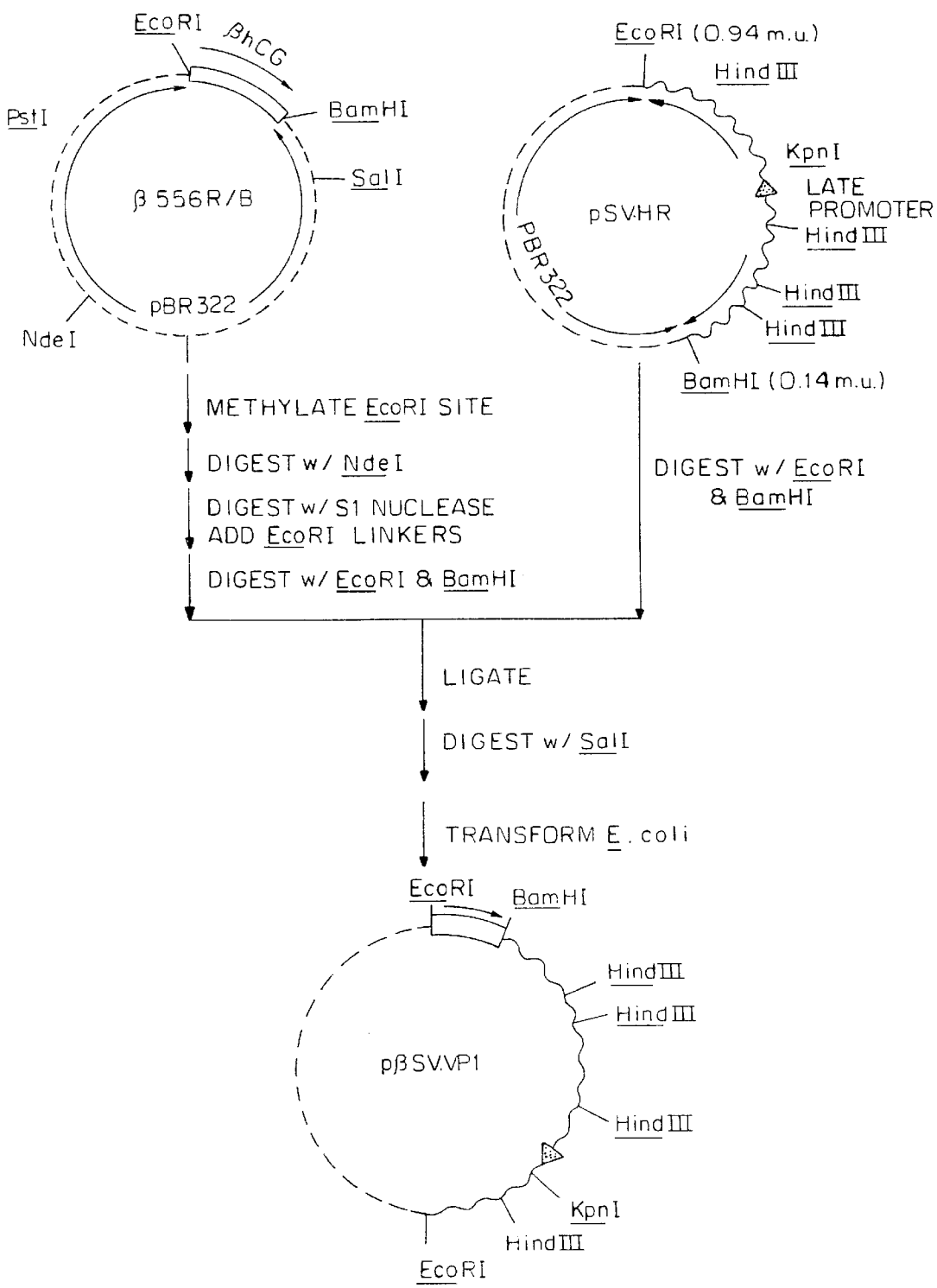
FIG. 2 is a diagrammatic illustration of the construction of plasmid pβ SVVPl, which incorporates the βhCG cDNA clone, regions of SV40 DNA and a portion of pBR322 including the region conferring resistance to ampicillin on host *E. coli*.

A 579 bp cDNA clone coding for β hCG was obtained from John C. Fiddes at Cold Spring Harbor Laboratory, Cold Spring Harbor, N.Y. (Fiddes et al., Nature 286:684, 1980). This fragment is ligated at each end to synthetic BamHI linkers. After digestion with HgaI restriction enzyme, the ends are filled in with Klenow DNA polymerase and synthetic EcoRI linkers are ligated on so that an EcoRI site is about 10 bp 5' to the ATG codon of the signal peptide coding sequence. A BamHI site is about 60 bp 3' to the nonsense codon marking the end of the coding sequence. Referring to FIG. 2, this 556 bp EcoRI-BamHI fragment is isolated and cloned into pBR322, between the EcoRI and BamHI sites, to give the plasmid p β 556 R/B.

In order to construct the plasmid pSVHR (FIG. 2), SV40 DNA is partially digested with HindIII to yield linear molecules, digested with nuclease S1 to make flush ends, ligated to synthetic EcoRI linkers and digested with EcoRI and BamHI. The fragment from 0.94 to 0.14 map units, containing the SV40 origin of replication and early region, is cloned into pBR322 as an EcoRI-BamHI piece.

Referring still to FIG. 2, the EcoRI site of the plasmid p β 556 R/B is methylated in a reaction catalyzed by EcoRI methylase, following which the plasmid is cut with NdeI. EcoRI linkers are ligated to the SI treated NdeI flush ends and activated by digestion with EcoRI, which is followed by digestion with BamHI.

The SV40 fragment of pSVHR from the EcoRI site to the BamHI site is isolated and ligated in a reaction mix containing the digestion fragments of p β 556 R/B. Following ligation, the mix is digested with SalI to eliminate plasmids which have re-inserted the EcoRI (NdeI) to BamHI piece of pBR322. E. coli is transformed with the digested ligation mix and p β SVVPl is identified and isolated.

Construction of Plasmid p α β SVVPl

Figure 3A:
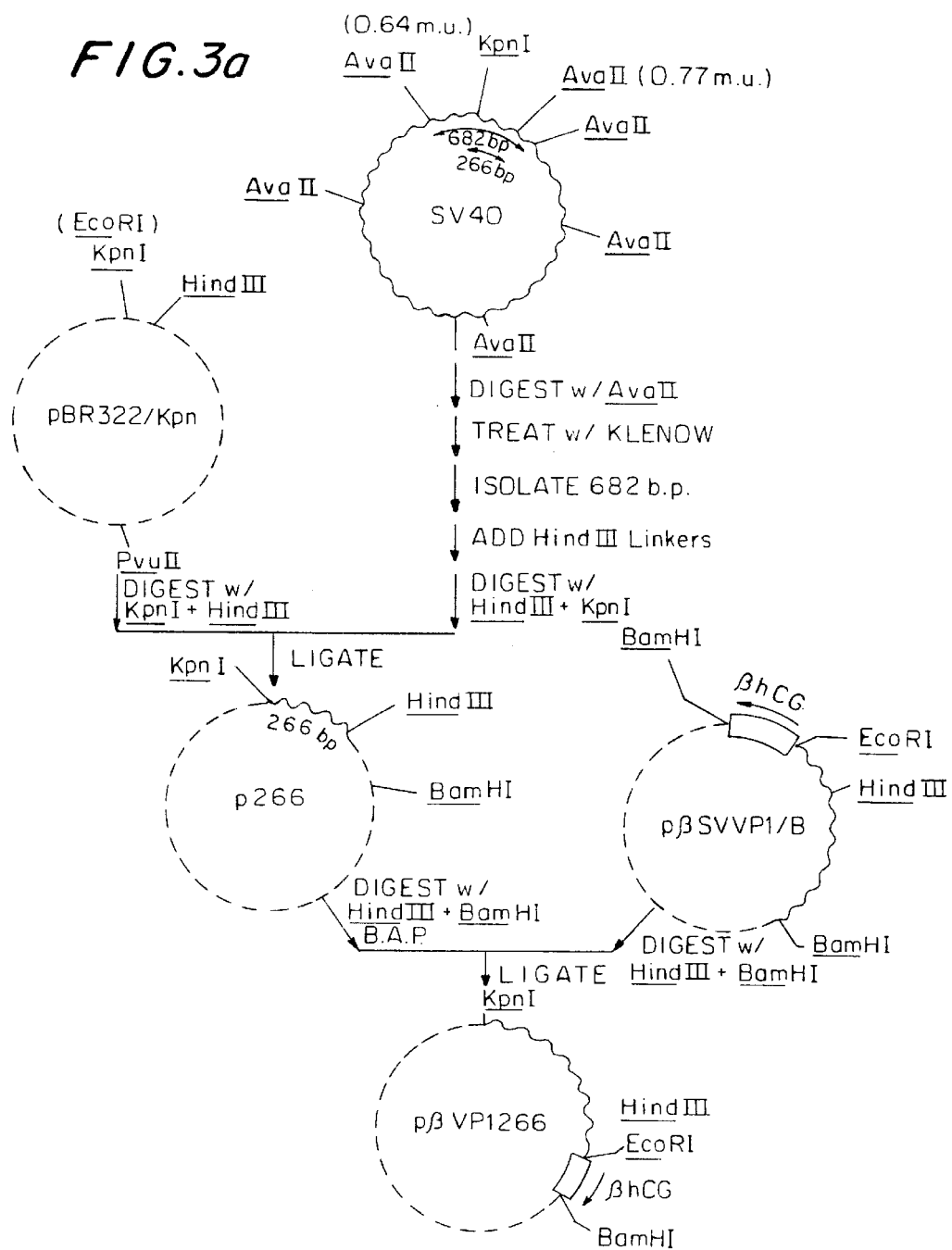
FIG. 3 is a diagrammatic illustration of the construction of the plasmid pαβ SVVPl in which the α and β hCG cDNA clones are inserted into SV40 DNA.
Figure 3B:
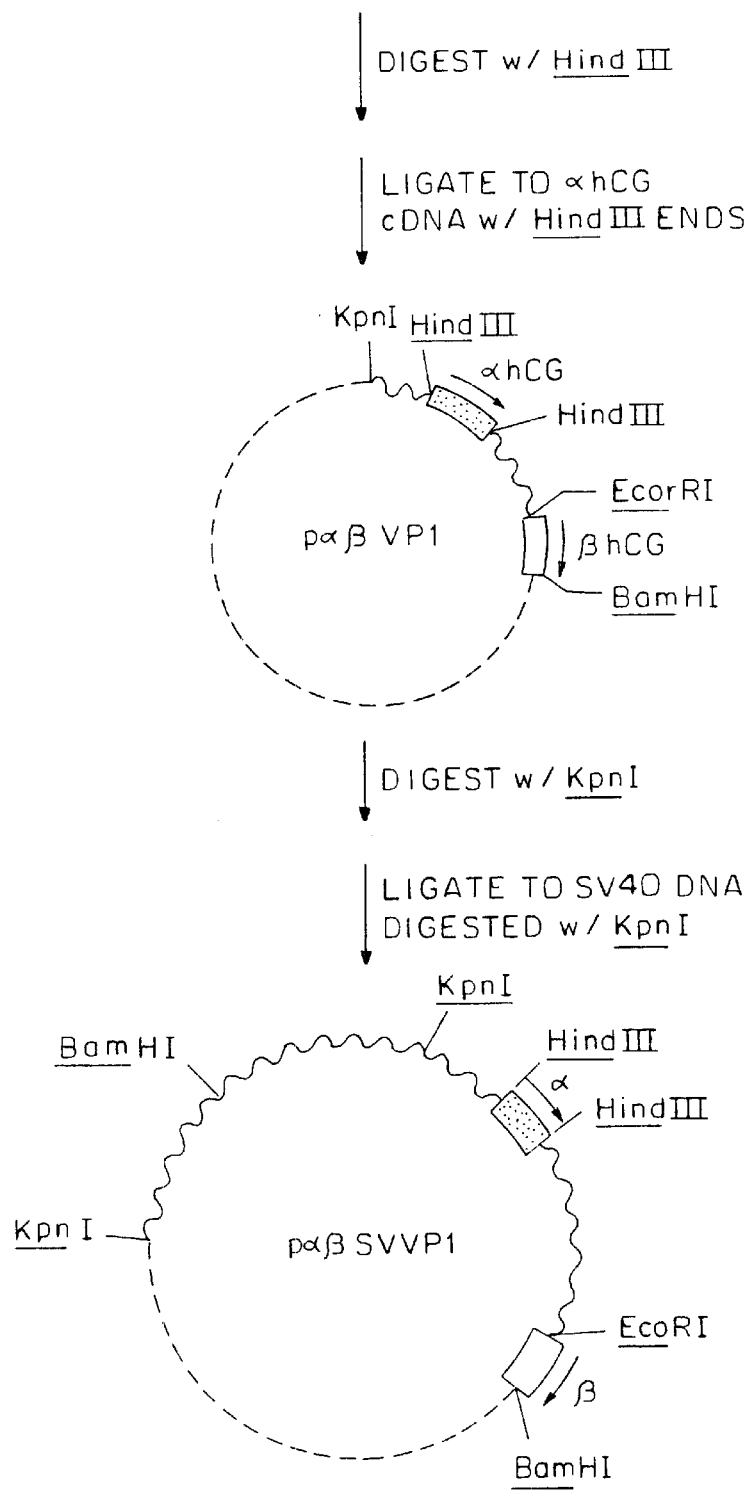

Referring to FIG. 3, pBR322/Kpn is derived from pBR 322 by inserting a KpnI linker into its unique EcoRI site, after this site is deleted by digestion with EcoRI, followed by digestion with S1 nuclease.

Referring still to FIG. 3, SV40 DNA is digested with AvaII. The staggered ends of the resulting fragments are filled in by Klenow DNA polymerase to form flush ends, and the mixture is then fractionated on a polyacrylamide gel. The 682 base pair fragment (0.64 to 0.77 map units) containing the origin of replication and the unique KpnI site is isolated from the gel, ligated to synthetic HindIII linkers, and digested with HindIII and KpnI.

The resulting fragments are ligated to pBR 322/Kpn. p266, which contains the 266 base pair KpnI-HindIII fragment, including the SV40 late promoter region, is isolated. p266 is cut with HindIII and BamHI, and treated with bacterial alkaline phosphatase.

Still referring to FIG. 3, p β SVVPI/B is constructed as follows: p β SVVPI (FIG. 2) is cut with EcoRI, followed by ligation to eliminate pBR322 sequences. Subsequently, this DNA is cut with BamHI and cloned into the BamHI site of pBR322.

The resulting plasmid, p β SVVPI/B, is then digested with HindIII and BamHI and the 1003 base pair HindIII-BamHI fragment is ligated into p266 to yield the plasmid p β VPl 266, in which the β hCG cDNA is positioned downstream from the SV40 late promoter in such a way that its RNA transcript would be spliced as if it were the viral VPl transcript.

The α hCG cDNA is inserted into p β VPl 266 as a HindIII fragment, which has been cut at its HindIII site and treated with bacterial alkaline phosphatase. E. coli transformants derived from this ligation are screened by restriction mapping, and plasmids are isolated that have the desired structure, in which the α hCG cDNA has replaced VP2 in the correct orientation, followed downstream by the β hCG cDNA, which has replaced VPl.

One such isolated plasmid, p α β VPl, is used to complete the construction of p α β SVVPl. The plasmid is cut with KpnI, and the full SV40 genome, cut with KpnI, is inserted by ligation into this site. Following transformation of E. coli, a plasmid with the required structure, p α β SVVPl, is isolated. This plasmid contains DNA encoding both the α and β subunits of hCG, and thus is capable of directing the expression, in host mammalian cells, of both subunits, whereby biologically functional, glycosylated heterodimeric hCG is produced (glycosylation occurs post-translationally).

Construction of pRF375 and pRF398

Figure 4:
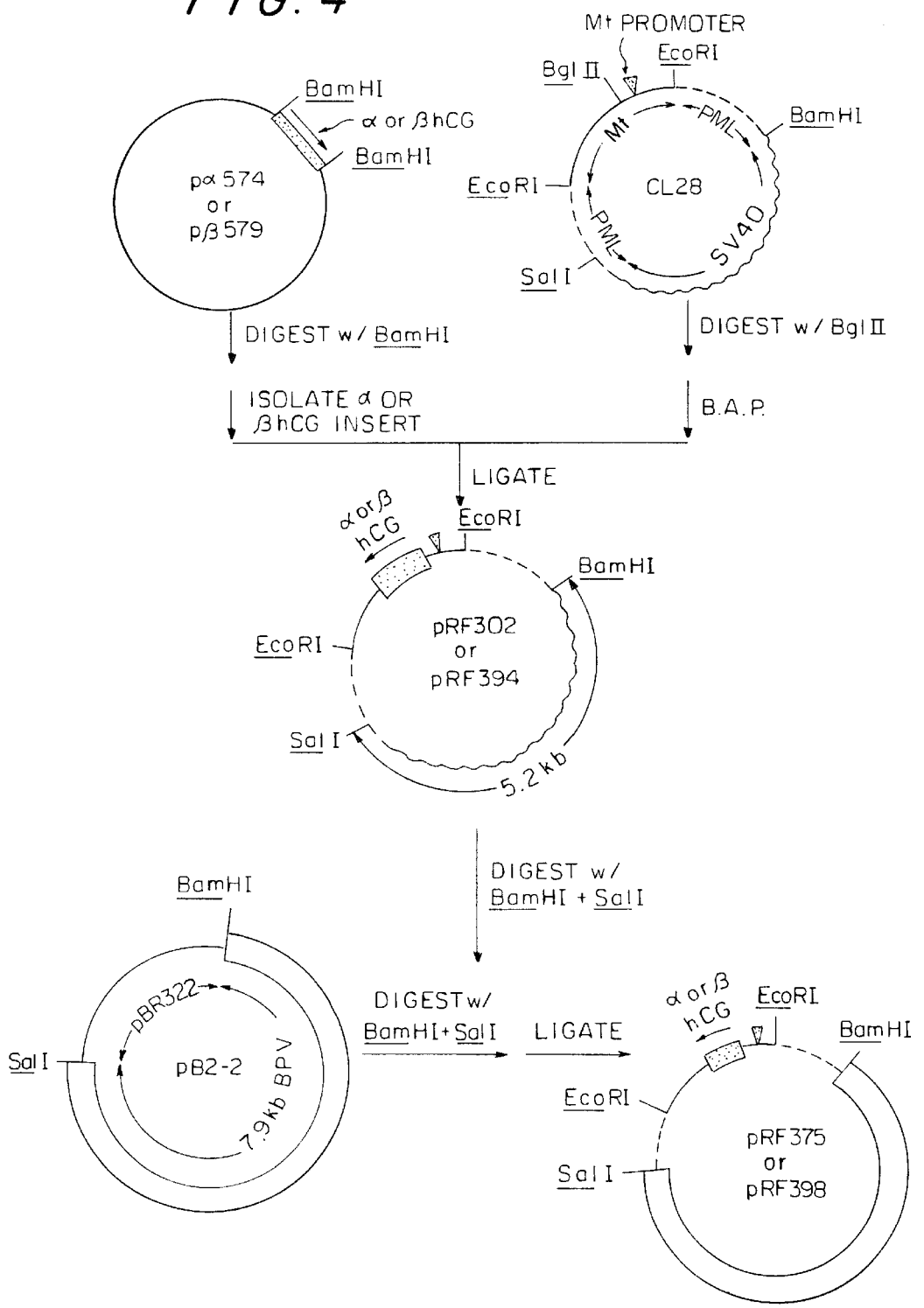
FIG. 4 is a diagrammatic illustration of the construction of the plasmids pRF375 and pRF398.

Referring to FIG. 4, the plasmid CL28 (identical to plasmid JYMMT(E); Hamer et al., J. Mol. Applied Gen. 1:273, 1983), containing the murine metallothionein promoter, SV40 DNA, and pBR322 sequences, is cut with the restriction endonuclease BglII. At this site are inserted cDNA clones of either α hCG or β hCG, containing untranslated regions of about 10 and 30 bp at their 5' and of about 220 and 60 bp at their 3' ends. These clones have been genetically engineered by the addition of synthetic BamHI linkers at their termini.

The resulting plasmids pRF302 (α) or pRF394 (β) are digested with restriction enzymes BamHI and SalI to release the SV40 DNA sequences.

Plasmid pB2-2, which contains the entire BPV genome, and some pBR322 sequences, is digested with BamHI and SalI to yield the BPV genome with BamHI/SalI ends; this fragment is ligated into pRF302 (α) and pRF394 (β) containing the metallothionein-hCG sequences.

Following transformation of E. coli, plasmids pRF375 and pRF398 are identified and isolated. They encode α hCG or β hCG, respectively, under the control of the mouse metallothionein promoter.

Construction of the Plasmid RF398 α $t_2$

Figure 5:
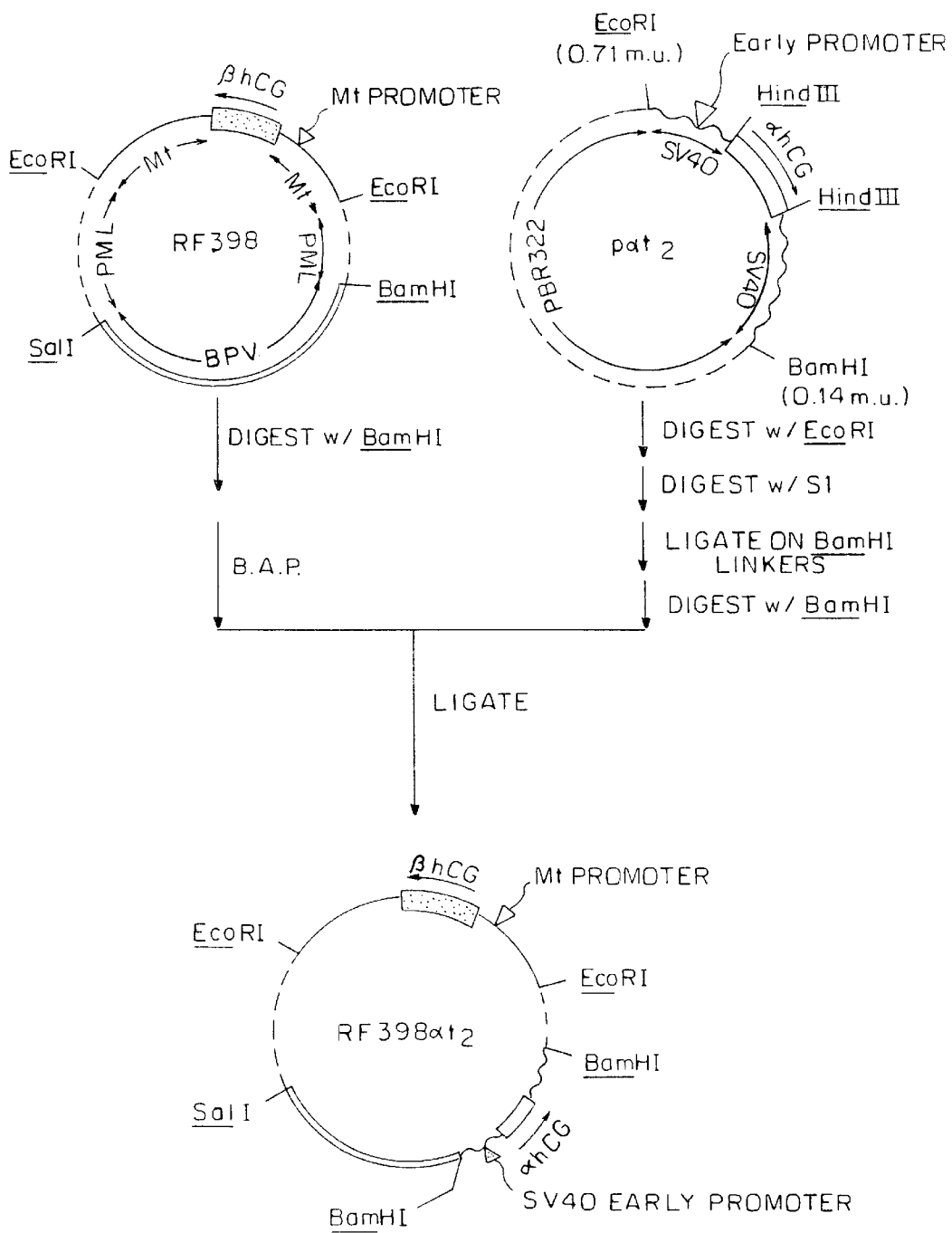
FIG. 5 is a diagrammatic illustration of the construction of the plasmid RF398 α $t_2$.

Referring to FIG. 5, the plasmid p α t2 is derived by cloning the α hCG 574 HindIII fragment into plasmid pVBt2 (Reddy et al., Proc. Nat. Acad. Sci. U.S.A. 79:2064, 1982). p α t2, which contains the α hCG cDNA under the control of the SV40 early promoter, is digested with EcoRI. The 5' overhangs are removed by S1 nuclease digestion prior to the addition of synthetic BamHI linkers by blunt end ligation.

Plasmid RF 398 (FIG. 4) is digested with BamHI and treated with bacterial alkaline phosphatase. The 1735 base pair BamHI fragment of p α $t_2$ is inserted in to RF398. The resulting plasmid RF 398 α $t_2$ is isolated from E. coli transformants. This plasmid thus has the β hCG cDNA in a transcriptional unit under control of the mouse metallothionein promoter and the α hCG cDNA in a transcriptional unit controlled by the SV40 early promoter.

EXAMPLE 2

Human LH (hLH)

RNA is prepared from human pituitaries by homogenizing 5 to 10 grams of the frozen glands in 20 ml of a solution containing 4 M guanidine thiocyanate, 1 M 2-mercaptoethanol, 0.05 M Na-acetate (pH 5.0), and 0.001 M EDTA. One g CsCl is added per ml of homogenate and the suspension is centrifuged at 2,000 rpm for 15 min. The supernatant is layered carefully over a 15 ml cushion of CsCl solution (containing 1.25 ml of 1 M Na-acetate (pH 5), 62.5 microliters of 0.4 M EDTA and 39.8 g of CsCl in a final volume of 35 ml) and centrifuged at 45,000 rpm in the Ti 70 rotor of a Beckman ultracentrifuge for 18–24 h at 20° C. The RNA visible in the gradient is removed with a syringe, diluted, and precipitated by the addition of two volumes of ethanol. Following three cycles of dissolution and reprecipitation, the RNA pellet is dissolved in $H_2O$ and brought to 0.01 M Tris-HCl (pH 7.5) and 0.5 M NaCl by the addition of concentrated stock solutions. The preparation is then enriched for poly $A^+$ mRNA by two passes over oligo dT-cellulose, as described above in the case of placental RNA.

A human pituitary cDNA library is constructed from the poly $A^+$ mRNA as described above for human placental poly $A^+$ mRNA except that both the large fragment E. coli DNA polymerase I and the avian myeloblastosis virus reverse transcriptase are used sequentially for second strand cDNA synthesis. The Klenow is used first. The reaction is stopped by phenol extraction. The aqueous phase of the centrifuged extract is applied to a 5 ml column of BioGel A-5m. Fractions containing high molecular weight material are pooled, concentrated, precipitated with two volumes of ethanol, dried, and dissolved in 100 mM Tris-HCl (pH 8.3), 10 mM $MgCl_2$, 140 mM KCl, 20 mM 2-mercaptoethanol, 1 mM of each of the four deoxyribonucleoside triphosphates, for reverse transcription. Reverse transcriptase is added to about 20 units per microgram of cDNA. Double stranded cDNA is then treated with nuclease S1, tailed, and cloned as described above.

Figure 6:
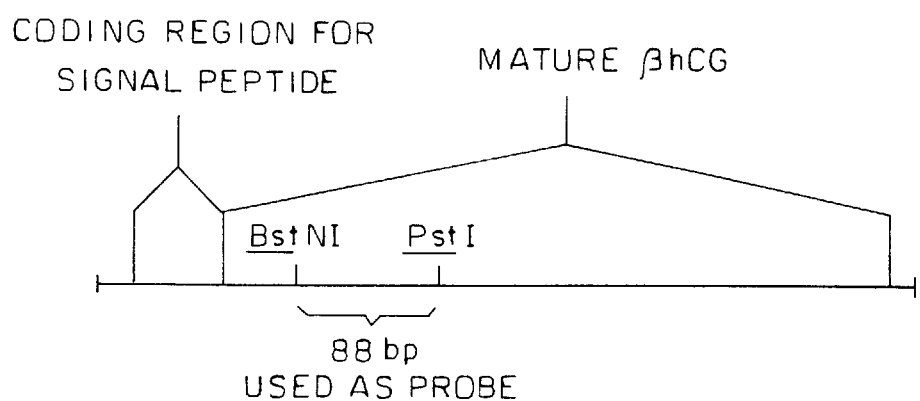
FIG. 6 is a diagram illustrating the location of an 88 bp probe within the β hCG cDNA clone.

Colonies from the cDNA library are grown on nutrient agar plates containing 25 micrograms per ml of tetracycline, transferred to nitrocellulose filters, and lysed in situ by treatment with 0.5 M NaOH, and neutralized with 0.5 M Tris-HCl (pH 7.4) containing 1.5 M NaCl. Liberated DNA is fixed to the filter by baking at 80° C. in a vacuum oven for 2 h. The filters are screened by hybridization to a $^{32}P$ labeled 88 base pair fragment of the β hCG clone corresponding to amino acids 16 to 45 of the mature hCG β chain, which has 29 of 30 amino acids in common with this region of the. LH polypeptide (FIG. 6). Hybridization is carried out overnight at 32° C. in 50% formamide, 0.75 M NaCl, 0.075M Na-Citrate (pH 7.0), 2.5% dextran sulfate, 0.1% polyvinylpyrollidone, 0.1 mg per ml bovine serum albumin, and at least $10^5$ cpm per filter of $^{32}P$-labeled 88 bp β hCG fragment. Filters are washed several times in 0.15 M NaCl, 0.015 M Na-citrate at 37° C. before autoradiography. One of the positive isolated clones LH12 (FIG. 7), is used further. LH12 is 365 bp long and includes sequences coding for 15 amino acids of the pre-β signal sequence plus 105 amino acids of the mature β LH polypeptide. Its nucleotide sequence is determined. Since the complete mature β LH is not coded by LH12, further screening of the human pituitary cDNA library is carried out using a 240 bp NcoI-PvuII fragment of LH12 (FIG. 7) as a $^{32}P$ labeled hybridization probe. The clone LH6 (FIG. 7) is isolated from this screening. LH6 contains the complete 3' end of β LH, including the region corresponding to the untranslated portion of the mRNA through 27 A residues of the poly A "tail" of the mRNA. No clones are found that extended further than LH12 in the 5' direction. DNA sequencing of the complete, combined mature β LH coding regions reveals two differences in the amino acid sequence of β LH from the published protein sequence data: position 42 is a methionine and position 55 is a valine. Also, the mature β LH contains 121 amino acids, based on the cDNA sequence.

Construction of Plasmid LH520H/B

Figure 7:
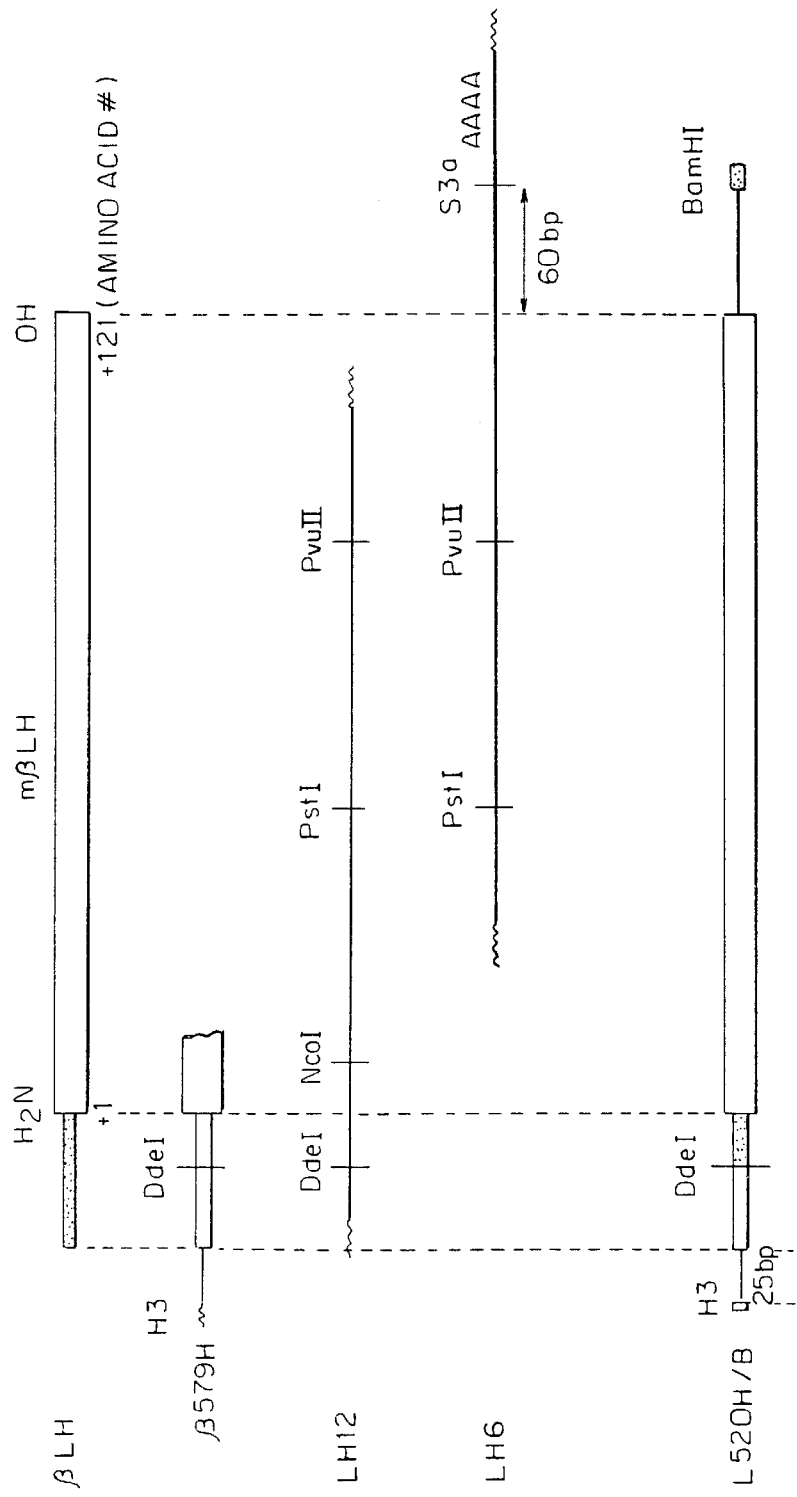
FIG. 7 illustrates the βhLH restriction map, and the pieces used in the construction shown in FIG. 8.
Figure 8:
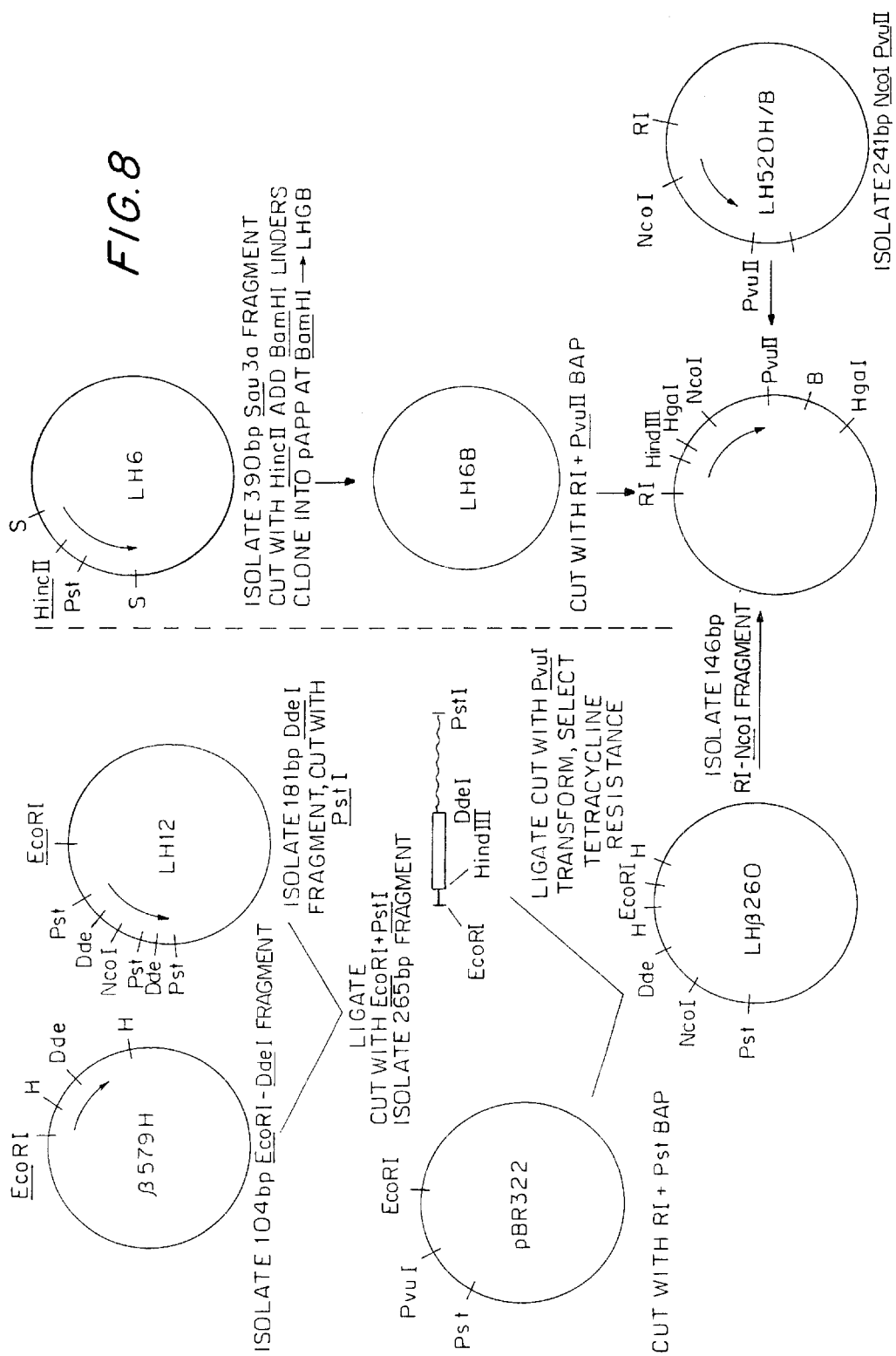
FIG. 8 is a diagrammatic illustration of the construction of a plasmid, LH520H/B, containing the complete mature βhLH cDNA clone.

A clone containing an intact signal peptide coding sequence and the complete mature β LH sequence is constructed as shown in FIG. 8, using the restriction fragment illustrated in FIG. 7. A 104 bp EcoRI-DdeI fragment is isolated from the plasmid β 579 H and ligated to an isolated 181 bp DdeI fragment, subsequently digested with PstI, from the LH12 plasmid. Following ligation overnight at 15° C., the ligation mix is digested with EcoRI and PstI and fractionated on a 7% polyacrylamide gel from which the desired 256 bp fragment is isolated. This fragment fuses the β hCG signal sequence to that of the pre-β LH in such a way as to provide a coding sequence for a 20 amino acid signal peptide.

The 256 bp EcoRI-PstI fragment is cloned into pBR322 digested with EcoRI and PstI so as to give the plasmid LH β 260. The 146 bp EcoRI-NcoI fragment indicated in FIG. 8 is isolated from a polyacrylamide gel and used later in the construction as described below.

The LH6 plasmid (FIG. 8) is digested with Sau3A and the 390 bp fragment is isolated by polyacrylamide gel electrophoresis. This fragment is then digested with HincII, ligated to BamHI linkers, digested with BamHI, and cloned into the plasmid pAPP at the BamHI site. pAPP is derived from pBR 322 by digestion with AvaI, filling in the 5' overhang with the dNTP's and the large fragment DNA polymerase I of *E. coli*, digestion with PvuII, and ligation to close the plasmid so as to eliminate the PvuII site. The plasmid LH6B, isolated from the ligation of the 340 bp BamHI fragment into the BamHI site of pAPP, is digested with EcoRI and PvuII, and treated with bacterial alkaline phosphatase. The fragments are ligated to a mixture of the 145 bp EcoRI-NcoI fragment of LH β 260, described above, and the isolated 241 bp NcoI-PvuII fragment from the plasmid LH12 shown in FIG. 8. The ligation mix is used to transform *E. coli* to ampicillin resistance. The plasmid LH 520 H/B is found among the transformants. LH 520 H/B contains a complete β LH coding sequence including a hybrid signal peptide sequence.

Construction of p α LHSVVPl

In order to express this pre-β LH clone in an SV40-based vector, as had been done for the pre-α and pre-β hCG clones described previously, it is desirable to place an EcoRI site very close to the ATG of the pre-β coding sequence. This is accomplished by digesting LH520 H/B with HgaI, filling in the 5' overhang, ligating on synthetic EcoRI linkers, digesting with EcoRI and BamHI, and cloning the isolated 496 bp EcoRI-BamHI fragment into pBR322 digested with EcoRI and BamHI and treated with bacterial alkaline phosphatase. The plasmid pLH496 R/B is isolated from *E. coli* transformed with this ligation mix and is used as the source of the 496 bp fragment to be expressed.

Figure 9:
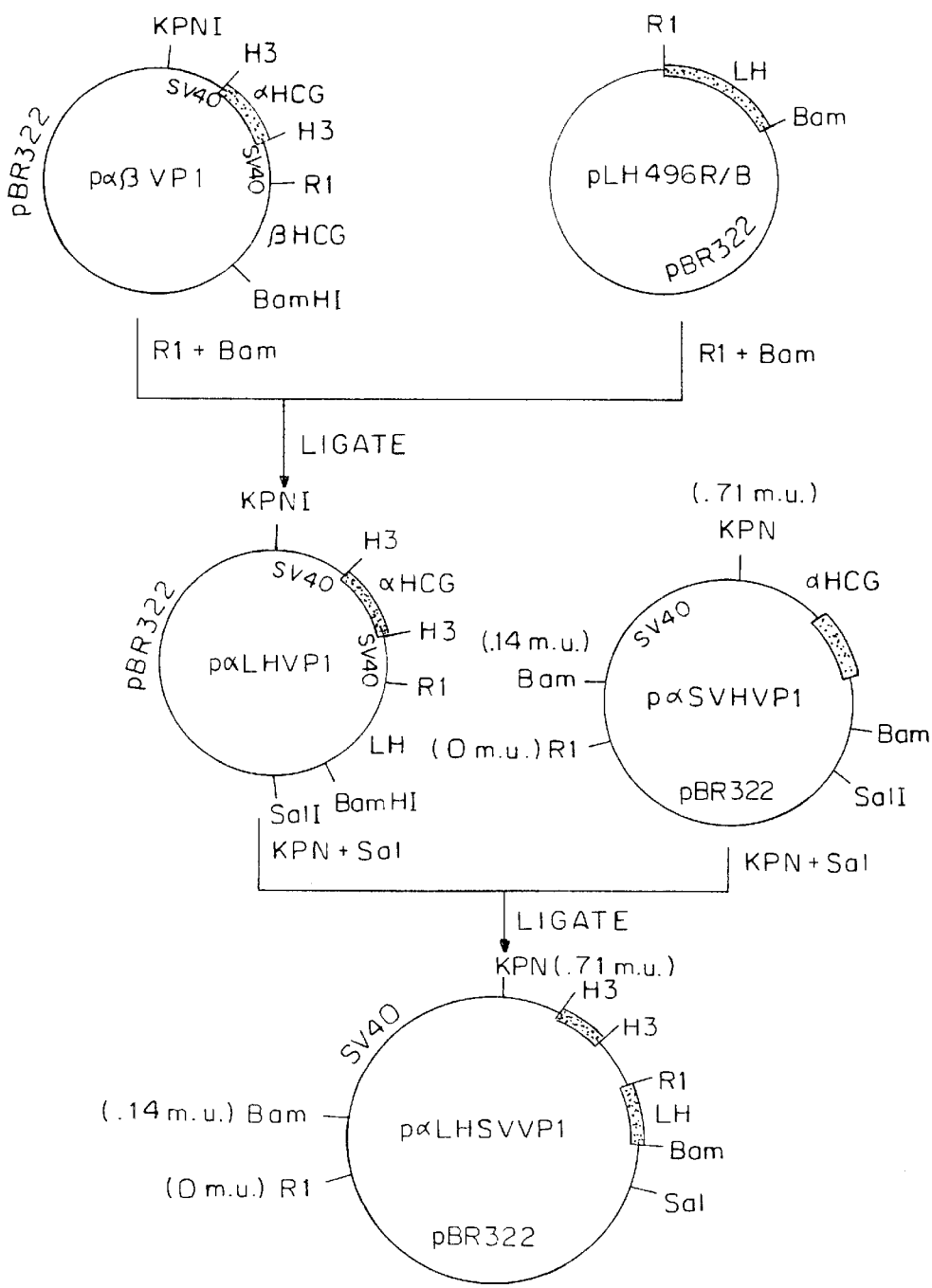
FIG. 9 is a diagrammatic illustration of the construction of the viral vector pα LHSVVPl.

The plasmid p α β VPl , whose construction and use in expressing both subunits of hCG is described earlier (FIG. 3), is digested with EcoRI and BamHI and ligated in a reaction mix containing the plasmid pLH496 R/B which had been digested with both of these enzymes (FIG. 9). The plasmid p α LHVPl is identified among the *E. coli* transformants. As shown in FIG. 9, the intact SV40 viral early region is taken from p α SVHVPl (FIG. 1) and inserted by ligation as a KpnI-SalI fragment into p α LHVPl which had been digested with KpnI and SalI to give the plasmid p α LHSVVPl . By cutting this plasmid with BamHI and religating, the virus a LHSVVPl is formed. This virus contains cloned cDNAs for the common (to LH and hCG, as well as FSH and TSH) α subunit and the specific β LH subunit under control of the SV40 late promoter. The cloned cDNAs are positioned in such a way that the common α insert replaced the viral VPl protein coding sequence and the β LH insert replaced the viral VP2 coding sequence.

Figure 10:
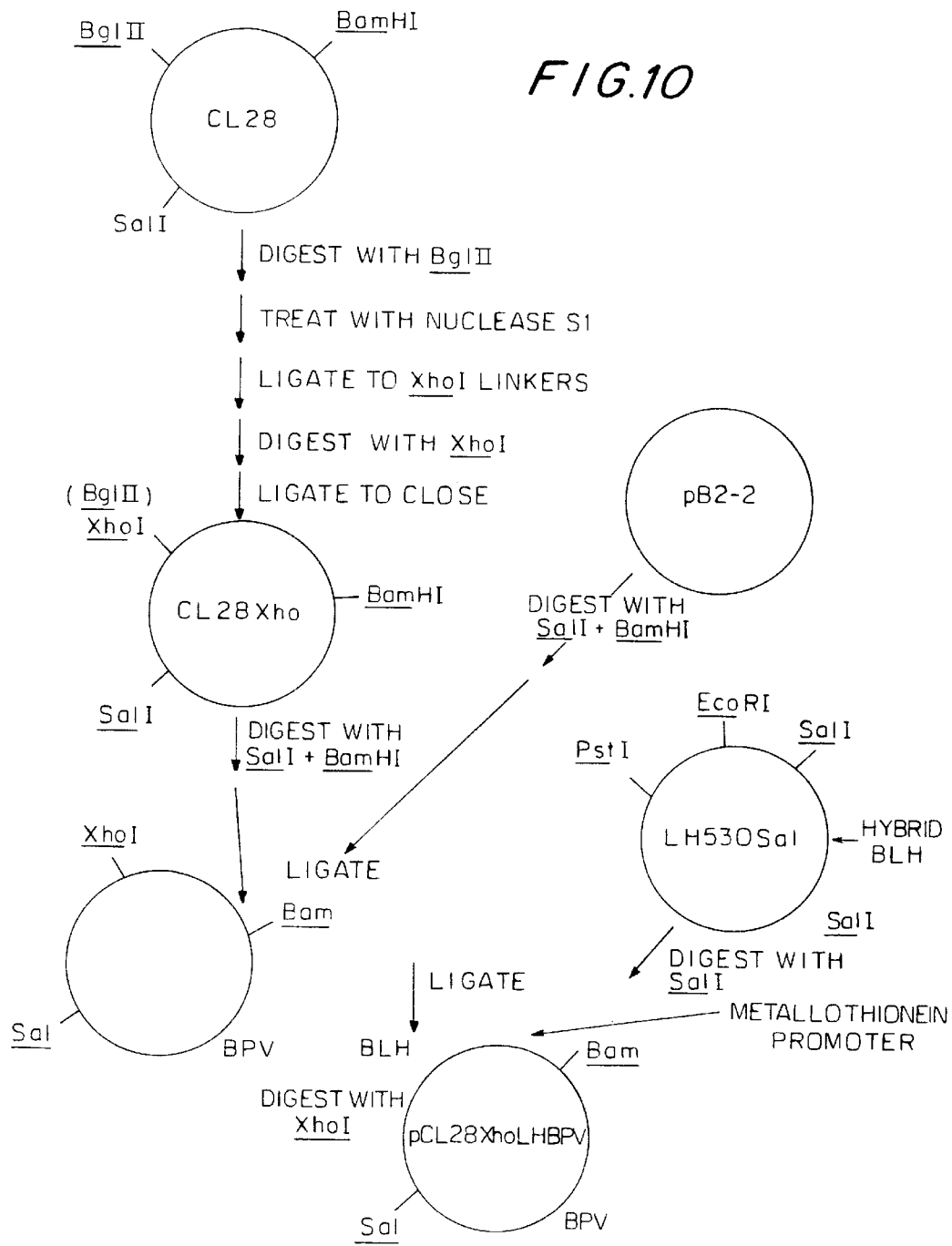
FIG. 10 is a diagrammatic illustration of the construction of the BPV-containing plasmid pCL28XhoLHBPV, encoding the β subunit of hLH.

Construction of pCL28XhoLHBPV

β LH cDNA (with β hCG 5' end of signal peptide) was inserted into a BPV-based expression system as follows. LH 520 H/B (FIG. 8) is digested with HindIII and BamHI, treated with the *E. coli* DNA polymerase (Klenow), ligated to synthetic SalI linkers, digested with SalI, and cloned into the SalI site of pBR322. The resulting plasmid, LH 530 Sal, is used as a source of the LH cDNA clone for insertion into the mouse metallothionein gene of the plasmid CL28 as described in FIG. 10.

CL28 is cut with BglII, treated with nuclease S1, and ligated to XhoI linkers. Following digestion with XhoI, ligation and digestion with BglII, *E. coli* is transformed with the reaction mix to give the plasmid CL28Xho. This plasmid is digested with BamHI and SalI and ligated to a BamHI plus SalI digest of the plasmid pB2-2 (FIG. 4) to give the plasmid CL28XhoBPV. The latter LH insert is then ligated into the XhoI site of CL28XhoBPV as a SalI fragment, since the 5' overhang of SalI digests is complementary to that of XhoI digests. Following digestion with XhoI to eliminate background, *E. coli* is transformed and the desired plasmid pCL28XhoLHBVP containing the (hybrid) pre-β LH insert, in a BPV-based plasmid, under control of the mouse metallothionein promoter, is isolated.

BOVINE HORMONES

EXAMPLE 3

Bovine LH and FSH (bLH, bFSH)

Bovine cDNA was synthesized from bovine pituitary mRNA by reverse transcription of poly $A^+$ RNA, treatment with NaOH to hydrolyze the RNA template, and second strand synthesis using reverse transcriptase. Following treatment with nuclease S1 and the EcoRI methylase, double stranded cDNA was ligated to synthetic EcoRI linkers, digested with EcoRI and ligated to the arms of the bacteriophage vector, λgt11. The recombinant phage were packaged in vitro by standard procedures and used to infect host *E. coli* cells to produce plaques. Clones were isolated by screening this cDNA library with appropriate probes.

The bovine α subunit cDNA was identified by hybridization of between 150,000 and 200,000 phage plaques with the 730 bp EcoRI fragment containing sequences from the bovine α coding region (obtained from R. Mauer, University of Iowa), which had been labelled by nick translation to a specific activity greater than $1\times10^8$ cpm per microgram.

The plaques to be screened were transferred to nitrocellulose filters, treated with NaOH, neutralized, washed with 2×SSC, baked in a vacuum oven at 80° C. for two hours, prehybridized and hybridized to the labelled, denatured α probe overnight. The filters were then washed twice with 1×SSC and four times with 0.25×SSC at 65° C. before being dried and autoradiographed at −70° C. for identification of positively-hybridizing plaques.

The complete nucleotide sequence of the coding region of the α cDNA was determined by use of both the chemical cleavage method of Maxam and Gilbert and the chain termination method of Sanger et al. The sequence of the coding region, including that coding for the 24 amino acid signal peptide, is given in FIG. 11.

In similar fashion, the cDNA for βLH is isolated and sequenced. A total of four clones were characterized, only one of which (LH7) contained the entire coding region at the 5' end of the clone. This clone, however, differed from the other three clones in that the triplet coding for amino acid 92 of the mature bLH β polypeptide was TCC (=Ser) rather than CCC (=Pro). Since LH's from other species contain Pro at this position, we spliced the 5' end of LH7 to the 3' region of the clone LH8 (one of the other four clones) in order to reconstitute a complete coding region with a proline codon corresponding to position 92 of the mature protein subunit. The splicing was carried out at a PvuII site located 14 base pairs 5' to the TCC codon in LH7. The nucleotide sequence of the bLH β subunit clone used in the expression system (see below) is shown in FIG. 12.

Identical procedures, to those described for bLH, were followed to identify bFSH clones, which were isolated by use of a porcine FSH probe (from NRRL B15793, see below). Because of abnormalities in each of the bFSH clones isolated (small deletions and a change in the region of the ATG initiator codon), it was necessary to splice together fragments to obtain a clone suitable for expression of the protein subunit. The DNA sequence of the bFSH β subunit are given in FIG. 13.

Figure 14:
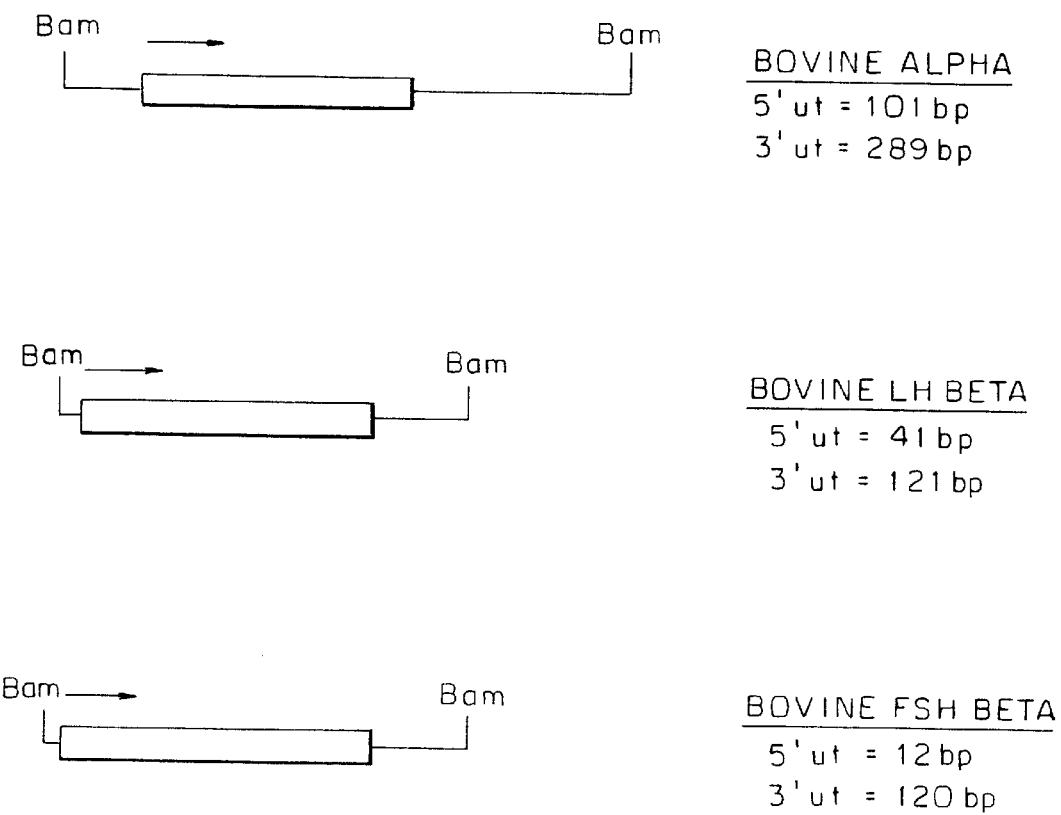
FIG. 14 is a diagram showing the cloned regions containing bovine hormone sequences.
Figure 15:
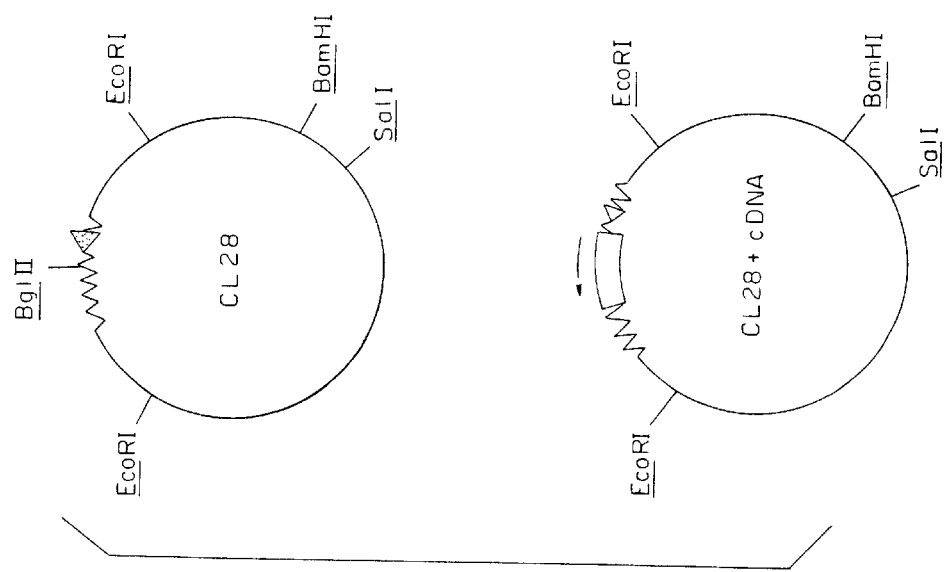
FIG. 15 is a diagrammatic representation of CL28 and bovine cDNA inserts in CL28.

Our first approach to genetically engineering the bovine gonadotropin cDNAs for expression was to construct separate expression plasmids for the α subunit cDNA and each of the β subunits cDNAs. BamHI linkers were ligated to flanking regions of each clone as shown in FIG. 14. These fragments were then inserted into the BglII site of the plasmid, CL28, shown in FIG. 15, so as to place each cDNA (shown as an open rectangle) under control of the mouse metallothionein promoter (shown in a triangle).

Figure 16:
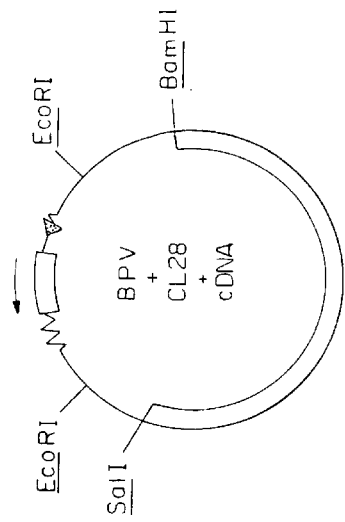
FIG. 16 is a diagrammatic representation of BPV-CL28 with bovine cDNA inserts.

The plasmid CL28 is shown before and after insertion of a bovine gonadotropin cDNA clone. Referring to upper part of FIG. 15, CL28 contains, in addition to a bacterial replication origin and a drug-reisitance marker (not shown), the mouse metallothionein gene (zig zag line), which has a unique cloning site (BglII) located just downstream of the metallothionein promoter (triangle). Referring to the lower figure, when a cDNA is inserted into the BglII site, a plasmid such as the one shown is obtained. The inserted cDNA, when it is positioned in the orientation given by the arrow above the box, is placed under control of the murine metallothionien promoter, which allows its expression in mammalian cells. Following these constructions, the entire Bovine Papilloma Virus (BPV) genome was inserted as a 7.9 kbp BamHI-SalI fragment into each plasmid (see FIG. 16). The BamHI and SalI sites are used for the insertion of the Bovine Papilloma Virus (BPV, large open rectangle) genome as shown in FIG. 16.

These plasmids allow expression of bovine gonadotropin cDNA in mouse C127 fibroblast cells. The BPV portion allows the plasmid to replicate in C127 cells and frees them from contact inhibition of growth so that permanent lines expressing the product encoded by the cDNA may be obtained.

Figure 17:
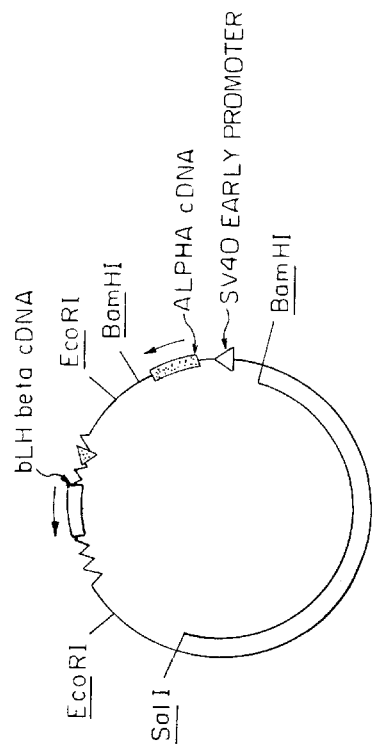
FIG. 17 is a diagrammatic representation of BPV-CL28 with α and β bovine cDNA inserts.

Another set of constructions, shown in FIG. 17, was carried out for the expresion of bLH. In addition to the features described above, this plasmid contains a second transcriptional unit in which the α cDNA has been placed between the SV40 early promoter (open triangle) and a strong transcriptional termination signal also derived from SV40. A single such plasmid will determine the production of both subunits, α plus bLH β, or α plus bFSH β. The α subunit cDNA is inserted into a site between the SV40 viral early promoter and the strong transcriptional termination region also derived from the SV40 virus. The entire unit is inserted as a BamHI fragment as shown in FIG. 17.

PORCINE HORMONES

EXAMPLE 4

Porcine LH, FSH (pLH, pFSH,)

The cDNA for the common α subunit of the porcine gonadotropins was isolated from a cDNA library constructed in the *E. coli* plasmid, pBR322, by G/C tailing into the PstI site in the β-lactamase gene.

Pituitaries from freshly slaughtered swine were quick-frozen in liquid nitrogen and stored at −70° C. until use. Total RNA was prepared from the frozen glands, after pulverization, by-extraction in (1:1) phenol: 100 mM Na-acetate (pH 5.5) at 65° C. Following separation of the phases by low-speed centrifugation, the organic phase was re-extracted with fresh acetate buffer as above and the resulting aqueous phase was pooled with the first. RNA was precipitated by the addition of 2.5 volumes of ethanol at −20° C. Redissolved total RNA was separated into poly A$^-$ and poly A$^+$-enriched fractions by chromatography on oligo (dT)-cellulose. The poly A$^+$-enriched material was precipitated with ethanol, washed with 70% ethanol and dried under vacuum.

First strand cDNA synthesis was carried out by standard protocols using the AMV reverse transcriptase (60 units) to reverse transcribe five micrograms ($\mu$g) of RNA in a reaction primed by two pg of oligo (dT) in a final volume of 20 microliters at 42° C. At the end of the incubation period, 0.01M Tris-HCl (pH 7.5) containing 0.001M EDTA (TE) was added and the mixture was extracted with an equal volume of phenol. The organic phase was re-extracted with TE and extracted once with chloroform. Three microliters of 0.25% acrylamide were added as carrier and nucleic acid was precipitated by the addition of 600 microliters of ethanol and 150 microliters of 4M $(NH_4)_2$-acetate and left overnight at −20° C.

Second strand synthesis was performed by the RNAase H method, which eliminates the need for treatment with S1 nuclease. The RNA-cDNA hybrid formed in the first reaction (above) was incubated for 60 min at 16° C. followed by 60 min at room temperature in the presence of 0.9 units of RNase H and 23 units of *E. coli* DNA polymerase I. Double stranded cDNA was extracted with phenol, precipitated with ethanol, washed, redissolved and tailed with dCTP by use of terminal deoxynucleotidyl transferase (40 units) in the presence of 1.4 mM $CoCl_2$.

Tailed cDNA was annealed with pBR322 DNA, which had been tailed with dGTP at its PstI site, and used to transform *E. coli* to tetracycline resistance.

Clones containing porcine α sequences were identified by hybridization to a bovine α cDNA (from pBR bov α 730 RI), which had been radioactively labelled by nick translation. One of these clones, p α 2B, was subcloned into pUC18 for sequencing. The results (FIG. 18) show it to be full length.

The cDNA for the βLH subunit was isolated from-another cDNA library. This library was constructed similarly to that described above. RNA was extracted from frozen porcine pituitary tissue by the guanidinium/cesium chloride method of Maniatis et al. supra, and poly(A)$^+$ RNA was isolated by two passages over oligo(dT)-cellulose. Two hybridization probes were used: a 320 bp NaeI-HinfI fragment (henceforth referred to as the 3' porcine probe) from an incomplete porcine LH β cDNA clone obtained from the library described above, using the bovine βLH cloned fragment as a probe, and the 120 bp 5' EcoRI-StuI fragment (henceforth referred to as the 5' bovine probe) isolated from bovine LH β cDNA.

First strand cDNA was synthesized from 10 ug porcine poly(A)$^+$ RNA using Moloney murine leukemia virus reverse transcriptase in the presence of oligo(dT) primer. Second strand DNA was synthesized by the method of Gubler et al., Gene, 25:263, 1983 in which RNase H was used to degrade the RNA strand and *E. coli* DNA polymerase I was used to sythesize the DNA replacement. 1.8 ug double stranded cDNA was obtained. The cDNA was C-tailed and annealed to PstI digested, G-tailed pBR322 (Bethesda Research Laboratories). Transformation of competent MC1061 cells with the annealed DNA resulted in a library of approximately 70,000 independent recombinant clones.

Screening the library for porcine LH β cDNA clones was done in two steps. First the entire library was screened at a high colony per plate density (7000 cfu/100 mm dish) with the 3' porcine probe. Approximately 600 duplicate positives were obtained. Twenty positives were selected for secondary screening. This was done by scraping the positive areas into broth, diluting the clonally mixed suspensions, and plating at a low colony per plate density (250–500 cfu/100 mm dish). Two replicas were hybridized to the 3' porcine probe and to identify the most complete clones, a third replica was hybridized to the 5' bovine probe. All 20 putative positives contained clones that hybridized in duplicate to the 3' porcine probe. 13 of the 20 also hybridized to the 5' bovine probe. Plasmid DNA was isolated from each of the 13 most complete clones. Examination by restriction endonuclease analysis showed the cDNA inserts to be similar in size, ranging from 500 bp to 540 bp. All clones contained the internal PvuII site present in the original incomplete porcine LH β cDNA clone. The clone with the longest 5' PvuII fragment was selected for further subcloning and sequence analysis.

The complete sequence of the porcine LH β cDNA insert, with amino acid sequence depicted, is shown in FIG. 32. The cDNA represents 486 bp of transcribed porcine LH mRNA, but does not include the ATG initiator codon. The longest open reading frame is shown in the figure, and is 137 amino acids in length, encompassing the entire mature porcine LH β subunit and 16 amino acids of the secretory leader peptide. The DNA translation differs from the published protein sequence (Pierce et al., Ann. Rev. Biochem. 50:465, 1981) in 6 locations:

| Amino acid pos. | Protein sequence | DNA translation |
| --- | --- | --- |
| 58 | Arg | Val |
| 79 | Ile | Ser |
| 83 | Ser | Ile |
| 130 | Pro | Leu |
| 136–137 | — | Phe-Leu |
| 36 | Asp | Asn |

The porcine FSH β subunit was isolated from a third cDNA library, which was constructed similarly to that described above for the isolation of the α subunit, except that second strand synthesis was carried out using the Klenow fragment of the *E. coli* DNA polymerase in the hairpin-primed reaction, rather than by the RNase H method. Following second strand synthesis, the cDNA was treated with S1 nuclease to digest the closed end of the hairpin; tailing, annealing and transformation of *E. coli* were performed as described above.

Figure 19:
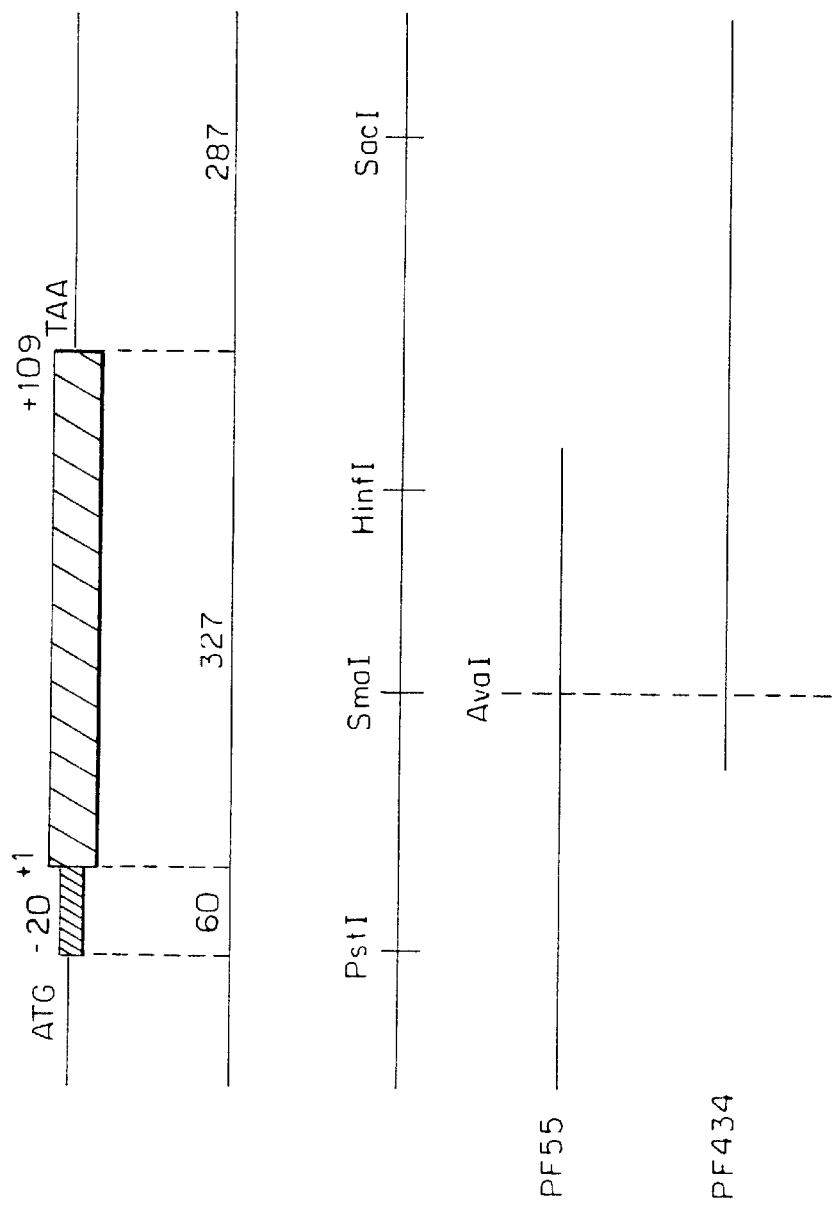
FIG. 19 is a diagrammatic representation of the cDNA clones isolated from around the porcine βFSH region.

Screening for the pFSH β subunit was carried out by using two synthetic DNA fragments, each of which was 45 base pairs in length, corresponding to amino acids 57–71 and 74–78 of the mature protein sequence (Pierce et al., An. Rev. Biochem. 50:465, 1981). The DNA sequences were chosen according to the codon usage method of Jaye et al., Nuc. Acid Res. 11:2325, 1983. Two clones were isolated from this screening, pF55 and pF434. As shown in FIG. 19, these clones overlap. They were joined at the unique SmaI/AvaI site to construct a continuous coding sequence, shown in FIG. 20.

Construction of CL28-αBPV

The 608 base pair a cDNA was cut with NcoI at position 102 and DdeI at position 504. The ends of this fragment, which contained the entire coding region for the pre-α protein, were filled in using the Klenow fragment of DNA polymerase I and ligated to synthetic BamHI linkers. The Tinkered fragment was digested with BamHI and ligated into the BamHI site of pBR322. The recombinant plasmid was identified by restriction mapping and used as a source of BamHI-ended DNA for insertion into the plasmid CL28. In brief, the inserted cDNA to be expressed is cloned into a unique BglII site in the metallothionein gene of CL28. Plasmids containing inserts in the proper orientation are isolated and the BPV genome is then inserted as a 7.9 kb BamHI-SalI fragment, as described above.

Construction of CL28-FSH-BPV

Engineering of the pFSH 55/434 clone was a bit more complex. First a RsaI-SmaI fragment, extending from position 70 to position 261 was isolated and cloned into the unique SmaI site of pUC18. Inserts in the correct orientation regenerate the SmaI site. This plasmid was then cut with SmaI and SacI and ligated to a SmaI-SacI fragment (position 261-position 629 of the cDNA) isolated from pFSH 55/434. The recombinant plasmid was identified by restriction mapping and inserted into CL28 as a BamHI-Sau3A fragment (the BamHI site derives from the polylinker of pUC18, and the Sau3A site is located at position 605 of pFSH 55/434). BPV was then inserted into a plasmid containing the engineered pFSH cDNA in the correct orientation with respect to the metallothionein promoter to constitute the final expression vector used to transfect C127 mouse fibroblasts.

EQUINE HORMONES

EXAMPLE 5

Equine LH (eLH)

The first step in the production of equine LH β cDNA is the preparation of pituitary RNA. The pituitary gland was removed from the horse immediately after death. The pituitary (approx. 2 grams) was homogenized in a 1:1 mixture of phenol: 100 mM Na-acetate, pH5.2 containing 0.5% SDS at 65° C. The homogenized tissue was incubated at 65° C. for 20 minutes with vortexing for 10 seconds every minutes. After quick cooling on ice, the phases were separated by centrifugation. The hot phenol extraction was repeated two more times followed by two extractions with chloroform:isoamyl alcohol (24:1). The RNA was precipitated from the final aqueous phase by the addition of 2.5 volumes of ethanol.

PolyA$^+$ RNA was isolated from the total equine pituitary RNA by oligo-(dT) cellulose chromatography. The RNA was passed over the oligo-(dT) column in 10 mM Tris-HCl, pH7.5, 0.5M NaCl. After several washings with this buffer solution, polyA$^+$ RNA was eluted with 10 mM Tris-HCl, pH7.5, 1 mM EDTA, 0.05% SDS. The chromatography was repeated and the final eluate precipitated with ethanol.

The equine cDNA library was constructed by conventional techniques. The first strand cDNA was synthesized by reverse transcription of pituitary polyA$^+$ RNA using the enzyme AMV reverse transcriptase. Second strand synthesis was carried out by sequential reactions with the Klenow fragment of *E. coli* DNA polymerase and AMV reverse transcriptase. The resulting hairpin loop was cleaved by S1 nuclease digestion. The double-stranded cDNA was C-tailed by reaction with calf-thymus terminal deoxynucleotidyl transferase and annealed to pBR322 which had been cleaved at the PstI site and G-tailed. These recombinant plasmids were then used to transform *E. coli* MC1061 cells to generate a cDNA library. Transformants were selected on the basis of tetracycline resistance.

In order to identify the equine LH β clone, a 520 bp fragment of the above bovine LH β cDNA clone was used as a hybridization probe. The probe, radioactively labeled with $^{32}$p by nick-translation, was used to screen the equine cDNA library by the colony hybridization technique of Grunstein et al. (Proc. Nat. Acad. Sci. U.S.A. 72:3961, 1975). Pre-hybridization was carried out at 37° C. in 50% formamide, 5×Denhardt's, 5×SSC, pH7.4, 0.1% SDS, and 100 ug/ml *E. coli* tRNA. Hybridization was carried out at 37° C. with the same solution containing denatured probe at a concentration of 5×10$^5$ cpm/ml.

The filters were washed at 55° C. with 2×SSC, 0.01M Na$_2$PO$_4$, pH7.2, 0.1% SDS. The washed filters were exposed to Kodak film overnight at −70° C. with one intensifying screen.

Screening yielded one equine LH β cDNA clone (pBR322-eLH Pst) whose sequence is shown in FIG. 21.

Equine α was isolated by a similar method to that described above for βLH, except that a 730 bp EcoRI fragment of bovine α cDNA was used as a probe. The DNA sequence of the a is shown in FIG. 23.

Construction of CLSVLPX-eLH

CLSVLP is an expression vector constructed to make use of the SV40 late transcriptional signals and the SV40, T-antigen-dependent origin of replication.

An SV40 late transcriptional cassette was constructed by joining the SV 40 fragment from TaqI (0.56 m.u.) to Hind III (0.83 mu) to the SV40 poly A signal fragment which spans the region of SV 40 from 0.14 to 0.19 mu. To accomplish this, the Hind III site at 0.83 mu and the BclI site at 0.19 mu were changed to BglII sites by filling in the overhanging basis with Klenow and ligating BglII linkers. The two fragments were then joined at this BglII site. This cassette, which now has TaqI and BamHl, at the 5' and 3' ends respectively, was put into pML2 at the ClaI and BamHI sites. pML2 is a deleted version of pBR322; the deleted sequences include from 1120 bp to 2490 bp on the pBR322 map (Lusky et al., Nature 293:19, 1981).

Figure 22:
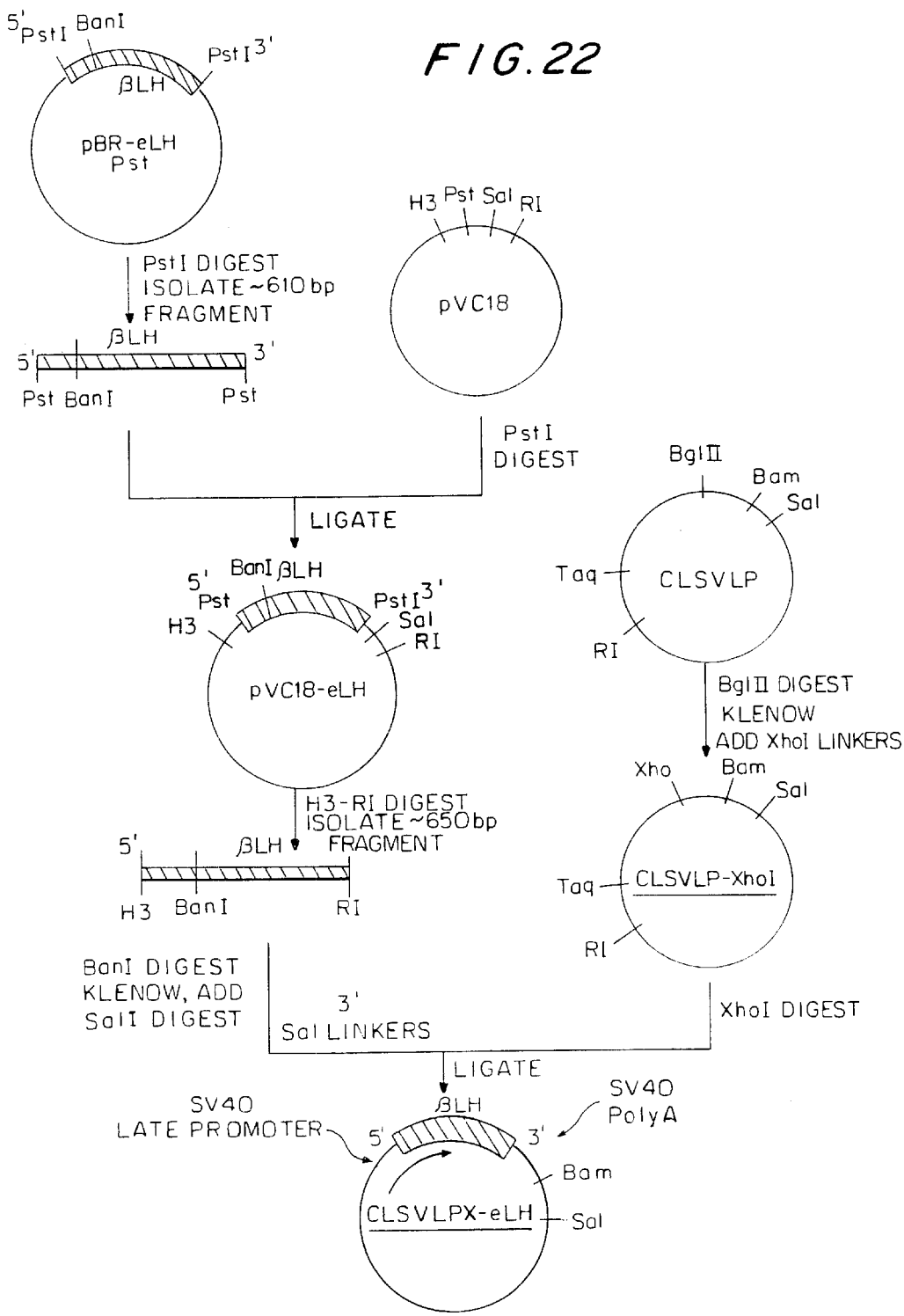
FIG. 22 is a diagrammatic representation of the construction of CLSVLPX-eLH.

Referring to FIG. 22, pBR322-eLH Pst was digested with Pst-1 and the 610 bp fragment was isolated. This Pst-1 fragment contains the entire coding sequences of equine β LH subunit. As an intermediate step, this PstI fragment was subcloned into the unique Pst I site in the multi-cloning region of pUC18 to create the vector, pUC18 eLH Pst. The orientation of the cDNA fragment with respect to the pUC18 is such that the unique EcoRI site in the multi-cloning region is at the 3' end of the cDNA. pUC18 eLH Pst was digested with HindIII and EcoRI, which flank the cDNA insert and the 650 bp fragment was isolated. This isolated DNA was subsequently digested with BanI, to make use of the unique BanI site 10 bp 5' to the ATG, filled-in with Klenow polymerase, and SalI linkers were added. A SalI digest was carried out and the mixture ligated to CLSVLP-Xho (which is simply CLSVLP with the BglII site changed to an XhoI site by the addition of XhoI linkers). Orientation was checked and the final DNA, CLSVLPX-eLH, was purified on CsCl gradients.

Construction of Plasmid CLSVLP-eα

Figure 24:
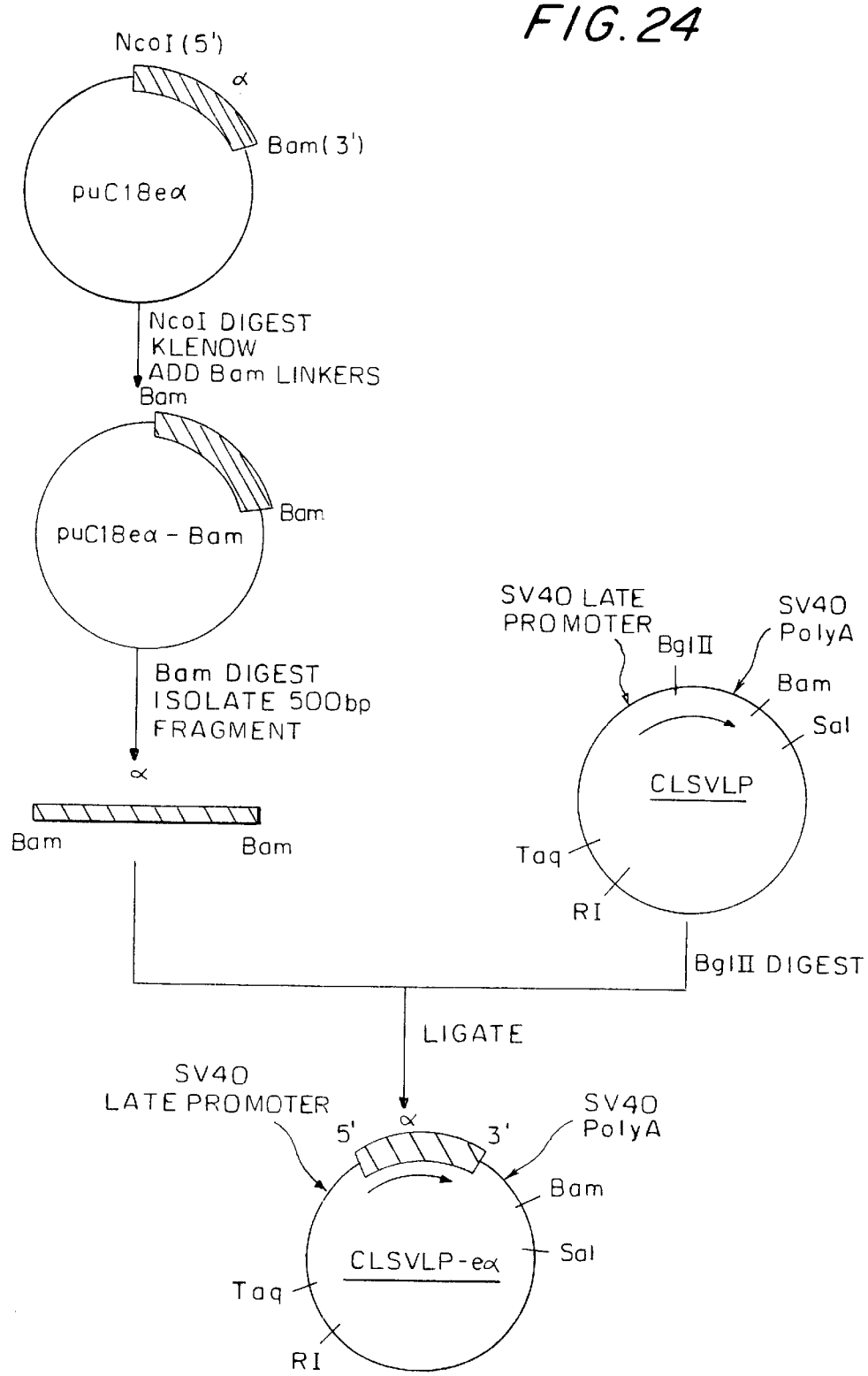
FIG. 24 is a diagrammatic representation of the construction of CLSVLP-eα.

The BamHl-NcoI fragment coding for eαLH was cloned into pUC18 by standard methodology to give pUC18eα. Referring to FIG. 24, pUC18e α DNA was digested with NcoI, filled in with Klenow polymerase, and BamHI linkers added. This construct, now called pUC18e α Bam, has two BamHI sites flanking the entire equine α cDNA region. pUC18e α Bam was digested with BamHI to isolate the cDNA, which subsequently was cloned into the unique BglII site of CLSVLP, and plasmids having the correct orientation (shown in FIG. 24), purified.

EXAMPLE 6

Equine FSH(eFSH)

An equine FSH β clone was isolated from a genomic DNA library constructed in the phage EMBL3.

The first step in the production of the equine genomic library was the preparation of equine DNA. Equine DNA was prepared from buffy coat cells which were isolated from total horse blood by centrifugation. The buffy coat cells were freed of contaminating red blood cells by lysis with freshly prepared red blood cell lysis buffer (10:1, 0.144 M $NH_4Cl$: 0.01 M $NaHCO_3$). The buffy coats were pelleted and resuspended in nuclei lysis buffer (0.4 M NaCl, 0.01M Tris-HCl, pH8.0, 0.002 M EDTA). SDS was added to 0.5% and proteinase K to a final concentration of 250 µg/ml. After overnight incubation at 37° C., the lysed cells were extracted two times with phenol and two times with $CHCl_3$. The DNA was ethanol precipitated, spooled, and resuspended at a concetration of 300 µg/ml in 0.01M Tris-HCl, pH8.0, 0.001 M EDTA at 4° C.

A genomic library was prepared in λ vector EMBL3 according to the method of Frischauf et al. (J. Mol. Biol. 170:827, 1983). Briefly, total horse DNA was partially digested with MboI to achieve a fragment length of 20 kb. The digested DNA was then treated with calf intestinal alkaline phosphatase, ethanol precipitated, and resuspended in 0.001 M Tris-HCl, pH7.5, 0.0001 M EDTA at a concentration of 0.5 µg/µl. EMBL3 vector DNA was digested to completion with BamHI and EcoRI. The DNA was phenol-extracted and precipitated with 0.6 vol of isopropanol. The DNA pellet was washed two times with 0.35 M NaAcetate (pH6):ethanol (1:25) and resuspended in 0.01 M Tris-HCl, pH7.5, 0.0001 M EDTA at a concentration of 0.5 µg/µl.

For ligation, vector and insert DNA were mixed in a 10:1 weight ratio (vector: insert) in 1×ligase buffer (10 mM Tris-HCl, pH7.6, 10 mM $MgCl_2$, 1 mM DTT, 0.5 mM ATP, 0.1 mg/ml BSA) and T4 ligase was added. Ligation was carried out overnight at 15° C.

Packaging of the ligated DNA was carried out using commerical packaging extract "Packagene" (Promega Biotech) and the resulting bacteriophage plated on the E. coli strain NM539. Bacteriophage were eluted with ice cold SM buffer and the resulting amplified library stored at 4° C. over $CHCl_3$.

Screening was carried by the method of Gruenstein et al., supra using a 520 bp coding region fragment of the above bovine FSH cDNA as probe. The probe was nick-translated. Pre-Hybridization was carried out at 37° C. in 50% formamide, 5×Denhardt's, 5×SSC, 0.1% SDS, and 11 µg/ml E. coli tRNA. Hybridization was carried out at 37° C. with the same solution containing denatured probe at a concentration of 5×10⁵ cpm/ml. Filters were washed at 45° C. in 2×SSC, 0,01 M sodium phosphate, 0.1% SDS and exposed to Kodak XAR film for two days at −70° with an intensifying screen.

Figure 25:
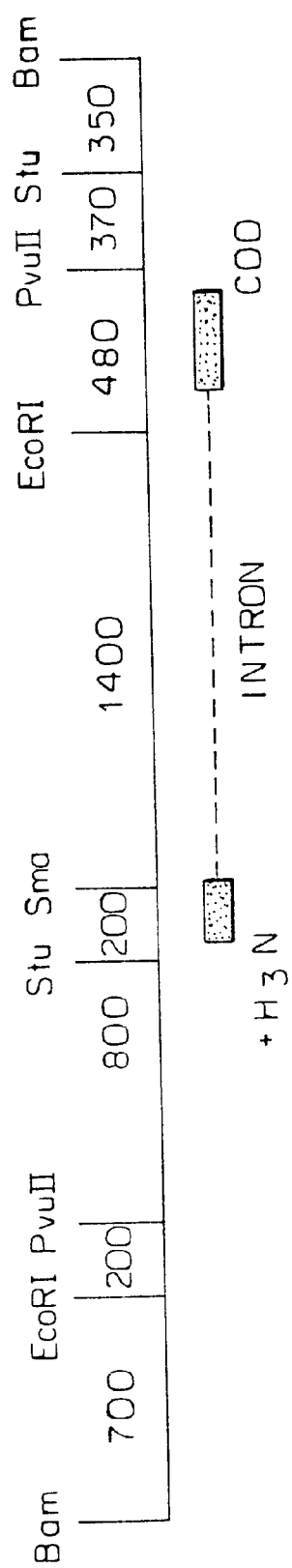
FIG. 25 is a diagrammatic representation of the equine βFSH clone, showing restriction endonuclease sites.

Screening yielded one recombinant bacteriophage containing the full-length equine FSH coding region. The restriction map of the 4.4 kb BamHl fragment of the remitting clone is shown in FIG. 25. The coding regions are shown below the map as dark boxes, which are connected by a broken line representing an intron.

Construction of Plasmid CLSVLP-βFSH

Figure 26:
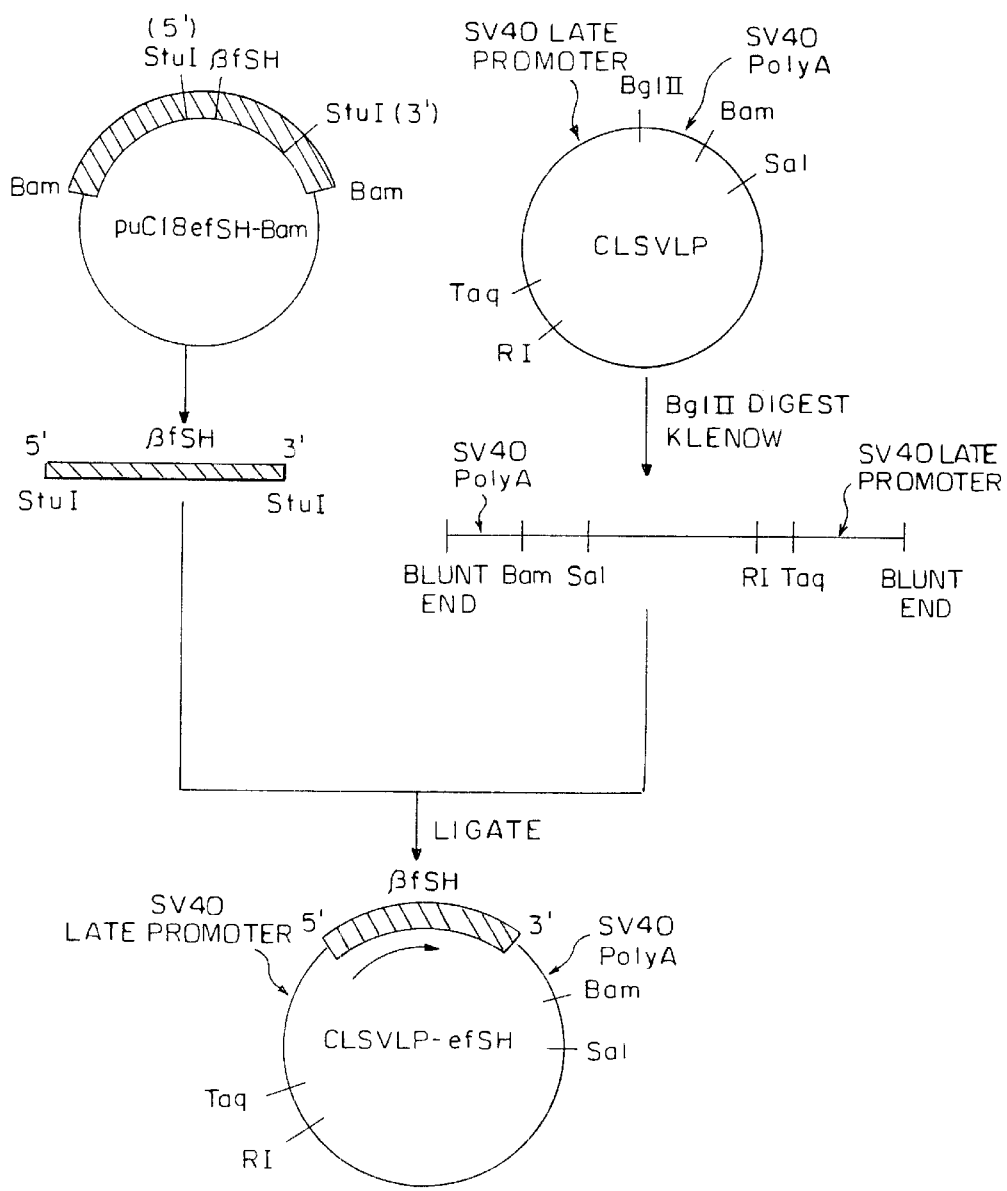
FIG. 26 is a diagrammatic representation of the construction of CLSVLP-eFSH.

Referring to FIG. 26, pUC18 eFSHBam contains the eFSH genomic DNA clone as a 4.4 Kb BamHI fragment. Partial sequencing revealed that the translational initiation codon (ATG) was about 25 bp downstream from a StuI site (FIG. 27). Restriction mapping showed at least one more StuI site about 2450 bp downstream from this first site. Partial sequencing suggested that the entire coding region for the β FSH subunit was present between the two StuI sites. pUC18 eFSHBam was digested with StuI (which leaves blunt ends) and a 2450 bp fragment was isolated on agarose gels. CLSVLP DNA was digested with BglII, filled in using Klenow polymerase, and ligated to the isolated StuI fragment. The correct orientation CLSVLP-βFSH was selected and DNA prepared.

Expression and Use

The above described vectors are useful for the expression of hormone subunits in appropriate cells. The incorporation of virus-containing vectors into eukaryotic cells for the production of a heteropolymeric protein is generally accomplished as follows. First, if the viral DNA and homopolymeric protein-encoding DNA are incorporated into a plasmid, which is maintained, in, say, E. coli, the plasmid sequences (e.g., the pBR322 sequences) are removed and the resulting DNA is ligated to form circular DNA including the viral region and the heteropolymeric protein-encoding sequence or sequences. This circular DNA generally does not contain all of the genetic information needed to produce a replicating virus, the other necessary sequences (e.g. those encoding coat protein) having been replaced by the heteropolymeric protein-encoding sequence or sequences. The circular DNA, minus the plasmid DNA, must be close enough in size to the naturally occurring viral DNA from which it is derived to permit the DNA to enter and replicate in appropriate host mammalian cells.

The circular DNA is used to transfect host cells in order to produce virus stock for later infections. Since some of the DNA necessary to produce virus is missing, the transfection must occur in conjunction with helper virus DNA encoding enough of the missing function to produce replicating virus.

Transfected host cells are grown and incubated until lysed by replicating virus. The resulting replicating virus stock, including helper virus, is then used to infect host cells for production of the heteropolymeric protein. Virus stock is maintained, since it generally needs to be reused to infect fresh batches of host cells, as each culture of infected, protein-producing host cells generally is eventually lysed by the virus.

The specific recombinant DNA sequences described above are used to transfect, and then infect, host cells, as follows. Again these examples are not meant to be limiting, those skilled in the art will readily see that other methods can be used for protein expression.

EXAMPLE 7
Human Hormones

The pBR322 sequences are removed from the above-described SV40-containing plasmids to produce transfecting viral DNA. In the case of p α SVHVPl and p β SVVPI, this is accomplished by digestion with BamHI, followed by ligation under conditions favoring circularization of the fragments to give (among other products) α SVHVPl and α β SVVPI. For p β SVVPI, digestion with EcoRI followed by re-ligation brings the SV40 late promoter and VP1 splice region into juxtaposition with the β hCG cDNA insert at the same time that it eliminates pBR322 sequences and forms β SVPl. At the same time, helper virus DNA, ptsA58 Bam (tsA58 SV40 viral DNA cloned into the pBR322 BamHI site), is cut with BamHI and ligated to obtain self-ligated circles. Analogous methods are used for the LH vectors. Separate virus stocks are prepared as described below.

The DNAs, which are cut and ligated as described above, are ethanol precipitated and dissolved in sterile water. Approximately 1 ug of ptsA58 Bam DNA and 10 ug of recombinant DNA (encoding α and/or β hCG or LH) are combined in a sterile test tube, mixed with 2 ml of TBS buffer (Kimura et al., Virogy 49:79, 1972) and 1 ml of 2 mg/ml DEAE-dextran solution and added to a monolayer of confluent monkey CV-1 cells previously washed twice with 10 ml of TBS in a T-75 flask. The cells are left at 37° C. for 1–2 hrs with occasional shaking, washed with TBS twice, fed with 10 ml of DMEM (Dulbecco's Modified Eagles Medium) containing 5% fetal calf serum, and left at 40° C. for 10–15 days. After complete cell lysis, the medium is transferred to a test tube, frozen and thawed five times, and centrifuged at 3,000 rpm for five minutes. The resulting supernatants serve as virus stocks for infection of fresh CV-1 cells.

To accomplish an infection, CV-1 cells are grown to confluence in a T-150 flask. 1 ml of one of the virus stocks (made as described above) is added to the flask and the cells are incubated at 40° C. for 5 days.

For mixed infections, CV-1 cells are grown to confluence in a T-150 flask. a SVHVPl and β SVPl viruses are mixed in a 1:1 ratio and 1 ml of the mixed virus is used to infect CV-1 cells at 40° C.

To produce heterodimeric hCG using a mixed transfection, five ug of each BPV plasmid, i.e., pRF375 (α hCG) and pRF398 (β hCG), are mixed and added to 0.5 ml of a 250 mM $CaCl_2$ solution containing 10 ug of salmon sperm DNA as carrier. This mixture is bubbled into 0.5 ml of 280 mM NaCl, 50 mM HEPES and 1.5 mM-sodium phosphate. The calcium phosphate precipitate is allowed to form for 30–40 minutes at room temperature.

24 hours prior to transfection, $5 \times 10^5$ cells of mouse C127 cells (available from Dr. Dean Hamer, National Cancer Institute, NIH, Bethesda, Md.) are placed in a 100 mm dish or T-75 flask. Immediately before adding the exogenous DNA, the cells are fed with fresh medium (Dulbecco's Modified Medium, 10% fetal calf serum). One ml of calcium phosphate precipitate is added to each dish (10 ml), and the cells are incubated for 6–8 hours at 37° C.;

The medium is aspirated and replaced with 5 ml of 20% glycerol in phosphate buffered saline, pH 7.0 (PBS) for 2 minutes at room temperature. The cells are washed with PBS, fed with 10 ml of medium, and incubated at 37° C. After 20–24 hours, the medium is changed and subsequent refeeding of the cells is carried out every 3–4 days. Individual clones are grown in T-25 flasks. After 7–21 days, cell clones can be transferred to larger flasks for analysis.

To produce heterodimeric hCG using a single transfection, plasmid RF398 α $t_2$ is employed in the same manner as the above two plasmids were employed for a mixed infection.

To make heterodimeric LH, plasmids PRF375 and pCL28XhoLHBPV are mixed, as described above in the case of hCG.

An interesting observation is that culturing cells containing β or β LH-encoding vectors alone, in the absence of α-encoding cells, produces practically no β subunit, while cells containing α and β-encoding sequences produce not only heterodimer, but free β subunit as well. This lends support to the notion that the production of both subunits in a single cell culture has the additional advantage of somehow permitting the presence of the α subunit to stabilize the β subunit.

EXAMPLE 8
Bovine Hormones

Figure 29:
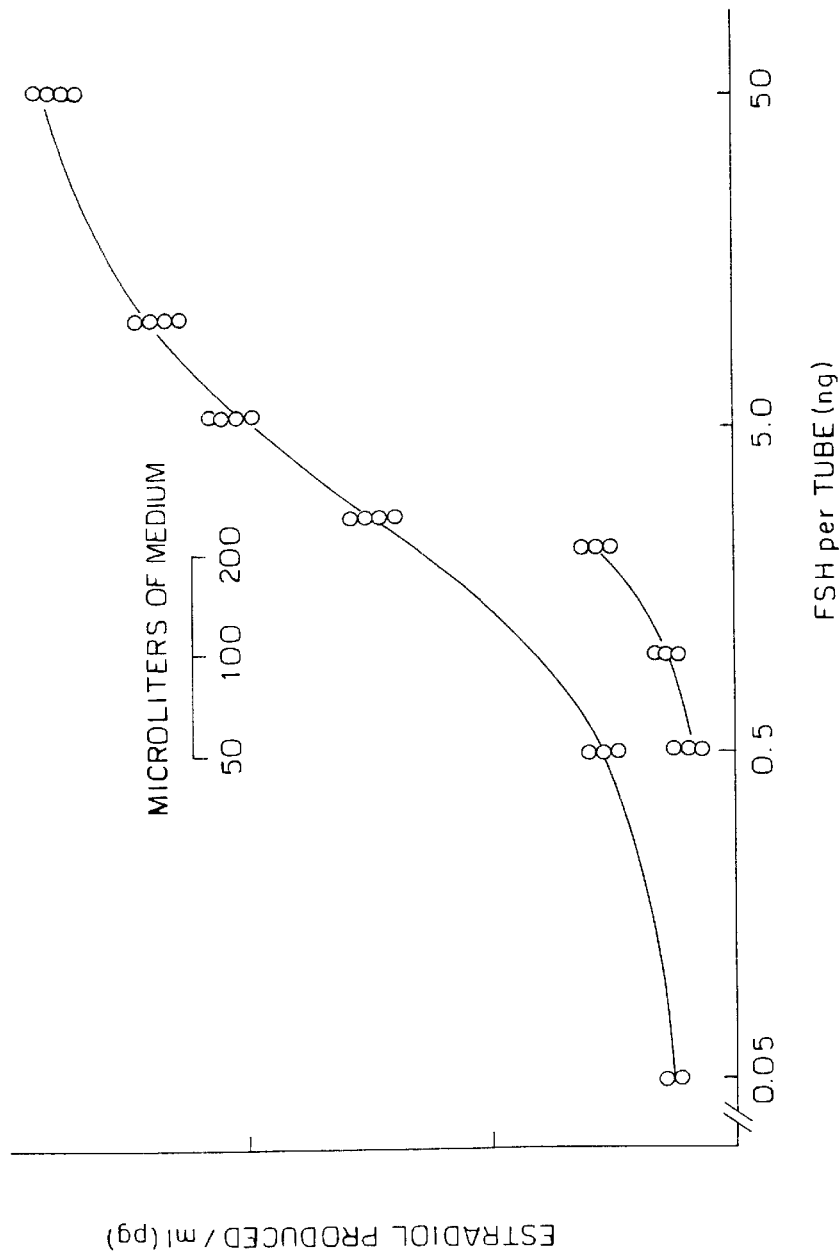
FIG. 29 is a graphical representation of activity of recombinant dimer FSH in samples of cell supernatants, measured by estradiol production.
Figure 30:
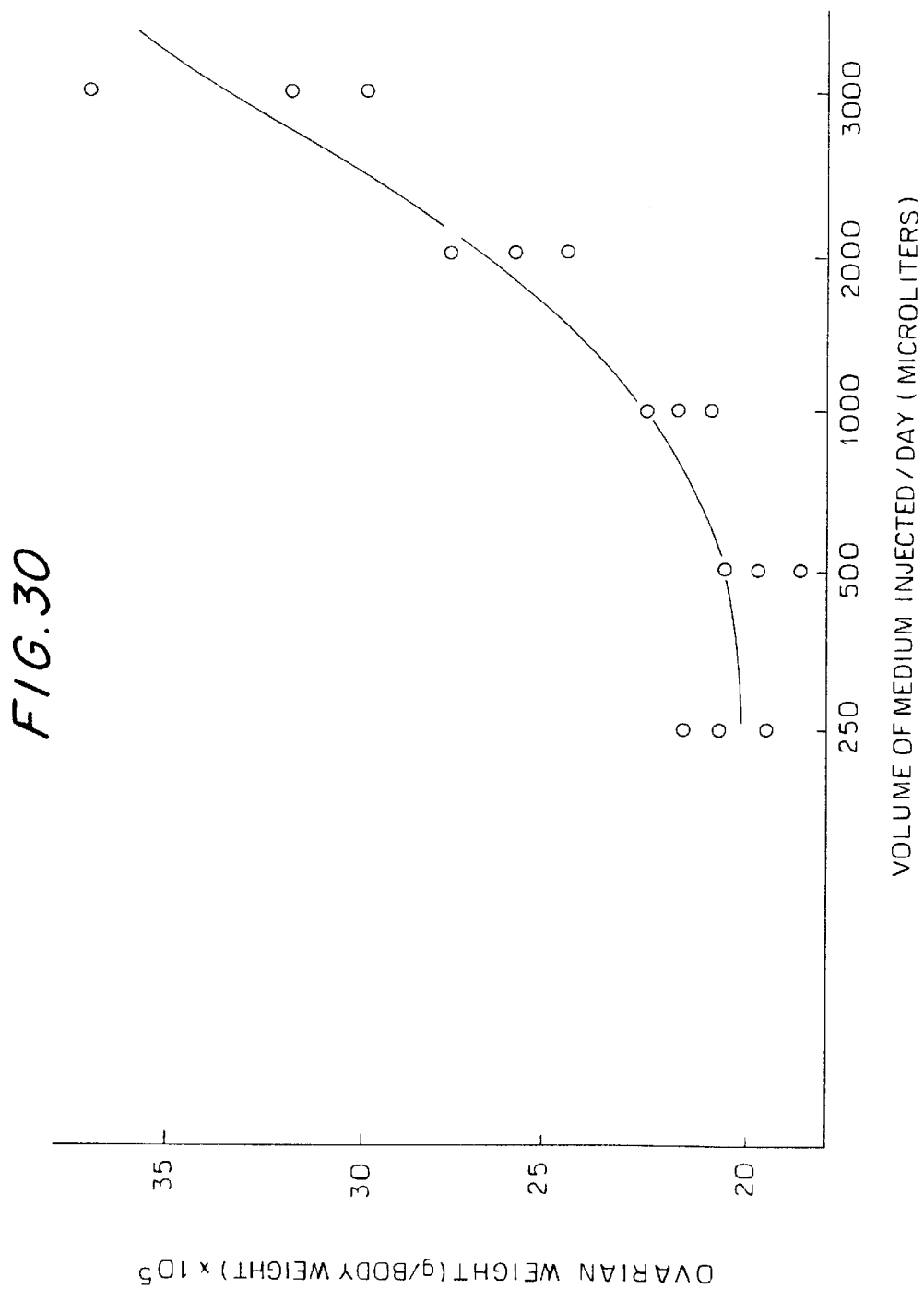
FIG. 30 is a graphical representation of activity of recombinant dimer FSH, measured by injection of samples, containing the hormone, into immature female mice and observing ovarian weight increase.

In order to derive cell lines producing bLH, the α-containing plasmid and the bLH β-containing plasmid were mixed together and introduced into mouse fibroblasts. Similarly, for the expression of bFSH, α-containing plasmid DNA was mixed with the bFSH β-containing plasmid and introduced into the mouse cells by the Ca-phosphate transfection procedure, described above. The mouse C127 fibroblasts were transfected with plasmids as described above and transformed cell lines derived from these transfections. Eighty-six cell lines were screened for bLH expression. Seven of these were selected for further characterization. For bFSH expression, eight of ninety-four lines were further characterized. Assays carried out both in vitro and in vivo demonstrated the biological activities of both bLH (FIG. 28) and bFSH (FIGS. 29, 30).

Figure 28:
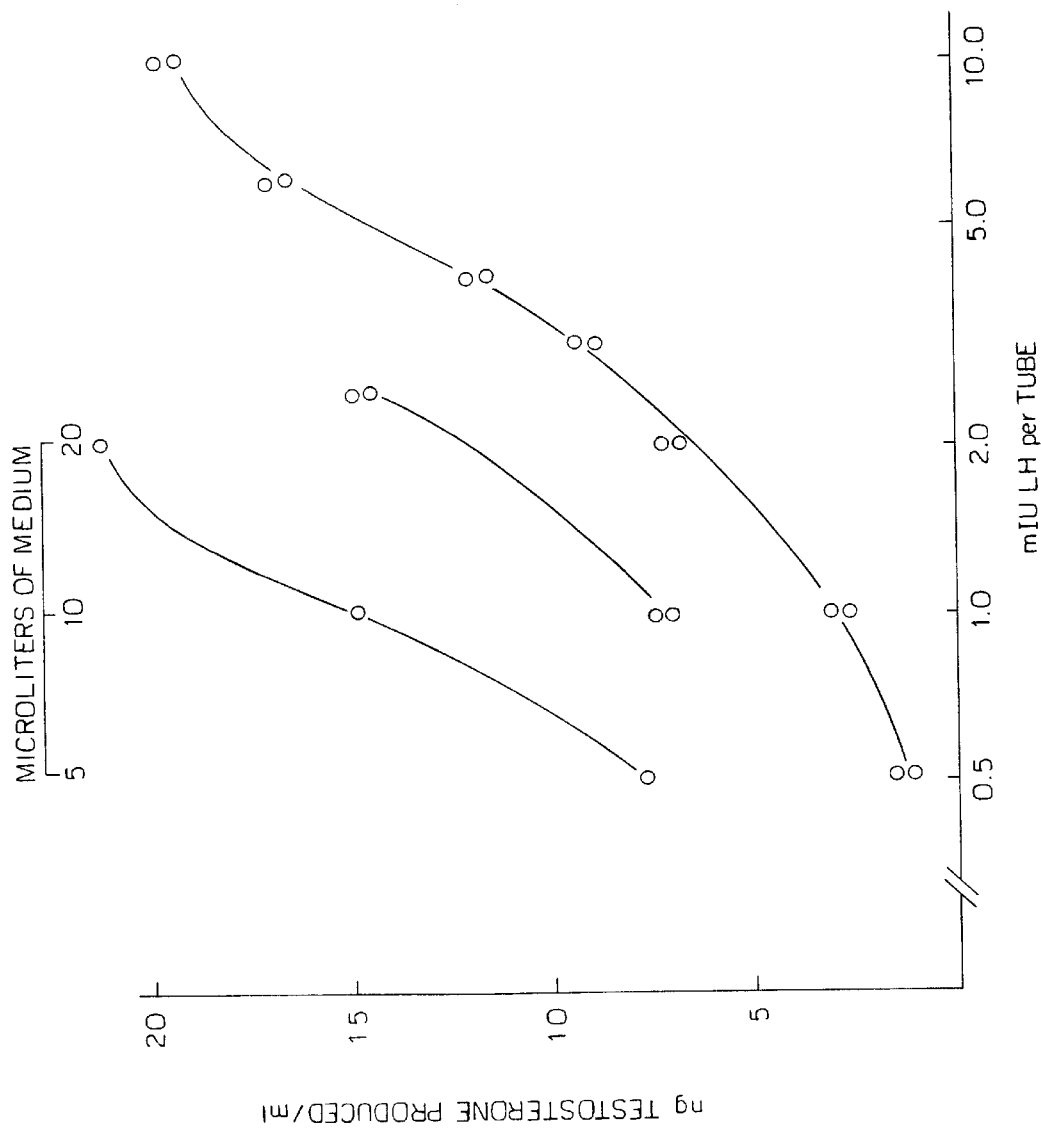
FIG. 28 is a graphical representation of activity of recombinant dimer LH, in samples of cell supernatants, measured by stimulation of testosterone.

Referring to FIG. 28, the in vitro bioassay of recombinant bLH is shown. This assay measures the ability of LH to stimulate testosterone secretion from an isolated preparation of steroidogenic cells (Leydig cells) prepared from rodent testes. Testes from mature rats are collected and the tunica albuginea is removed. The decapsulated testes are mechanically disrupted and the seminiferous tubules separated from the Leydig cells by filtration through nylon mesh. The Leydig cells, which pass through the mesh, are centrifuged at low speed and resuspended in culture medium for use. Each determination is carried out using a tube containing one million viable cells. Reference standard LH or different amounts of unknown are added to each tube. Following incubation at 37° C. for three hours, the cells are removed by centrifugation and the supernatants are assayed for testosterone by a specific radioimmunoassay. The standard curve is shown in open circles, while assays of tissue culture supernatants from lines expressing bLH from the cloned cDNAs are given in closed circles. The concentraton of bLH can be calculated from noting the number of microliters required to give a response equivalent to the known number of mIU of the LH reference preparation.

Results of in vivo bioassays are given in Table 1.

TABLE 1

| SAMPLE | Number | VOLUME INJECTED (mL) | UTERINE WEIGHT (mg ±SEM) |
|---|---|---|---|
| Control | 3 | 10 | 14.6 ± 1.6 |
| bLH Medium | 3 | 2 | 16.7 ± 2.9 |
| " | 3 | 5 | 21.2 ± 7.6 |
| " | 3 | 10 | 31.8 ± 9.3 |

Immature female mice (19–22 days) were injected i.p. with either control tissue culture medium or medium removed from cultures of a bLH-producing line as shown in the table. The indicated volumes were injected over a 72 h period in a series of six injections. At the end of the experiment, the mice were sacrificed and their uteri were carefully dissected out, blotted dry and weighted on an analytical balance.

Referring to FIG. 29, the in vitro bioassay of recombinant bFSH is shown. Suspensions of Sertoli cells were prepared from rat seminiferous tubules by treatment with collagenase and mechanical dispersion. The cells are pelleted by centrifugation and plated in microtiter wells at a density of $1 \times 10^5$ viable cells per well for 24 h. The culture medium is then removed and replaced with fresh medium containing androstenedione plus either a reference FSH preparation or sample of the cell supernatants to be assayed from bFSH production. Following a 24 h incubation period, the medium in each well is assayed from estradiol by radioimmunoassay. The presence of biologically active FSH stimulates the production of the enzyme aromatase by the Sertoli cells. Aromatase, which is induced by FSH in a dose-dependent manner, converts the androstenedione to estradiol. The standard FSH preparation generated the curve shown in open circles, while tissue culture supernatant from a bFSH-producing line gave the results shown in closed circles. The assay demonstrates in vitro bioactivity from the recombinant bFSH.

In vivo bioassay of recombinant bFSH was also performed (FIG. 30). Increased ovarian weight results from the action of FSH in stimulating follicular growth and development. Since the recombinant bFSH is free of LH activity, there is no need to employ hCG before the FSH-containing sample (Steelman and Pohley assay). The curve shown demonstrates the biological activity in vivo of the recombinant material.

EXAMPLE 9

Porcine Hormones

To produce cells which synthesize and secrete pFSH, C127 mouse fibroblasts were transfected with a mixture of two plasmids: the α cDNA in the metallothionein-BPV plasmid and the pFSH cDNA in this same type of construction, as described above. Fifty micrograms of each plasmid was added to 0.5 mL of a 250 mM $CaCl_2$ solution containing 10 mg of salmon sperm DNA as carrier. The mixture was bubbled into 0.5 mL of 280 mM NaCl, 50 mM HEPES and 1.5 mM Na-phosphate. The calcium phosphate precipitate was allowed to form for 30 minutes at room temperature.

Twenty-four hours prior to transfection, $5 \times 10^5$ mouse C127 fibroblasts were transferred to a 100 mm culture dish. Immediately before adding the exogenous DNA, the cells were fed with fresh medium (Dulbecco's Modified Medium, 10% fetal bovine serum). One mL of the calcium phosphate precipitate was added to each dish (10 mL), and the cells were incubated at 37° C. for 8 hours. The medium was then aspirated and replaced with 5 mL of 20% glycerol in phosphate-buffered saline, pH 7.0 (PBS) for two minutes at room temperature. The cells were washed once with PBS, fed with 10 mL of medium and incubated at 37° C. for 24 hours. At this time, the medium was changed, and subsequent refeeding was carried out every three days.

Expression of pFSH was determined by in vitro assay. Cell supernatants, potentially containing FSH, were collected and concentrated by dialysis against polyethylene glycol. These concentrated samples were then assayed for in vitro activity as follows: Immature female rats (21 days old) were injected with 5 IU of PMSG (pregnant mouse's serum gonadotropin) and killed 48 hours later. Their ovaries were removed and placed in ice-cold Medium 199. Granulosa cells were expressed from the ovarian follicles into McCoy's 5A medium with 4 mM glutamine and antibiotics. Approximately $0.25 \times 10^6$ cells per well were inoculated into microtiter dishes in a volume of 1 mL and samples to be assayed (the above cell supernatants) and standards were added in a volume of 0.3 mL.

Figure 31:
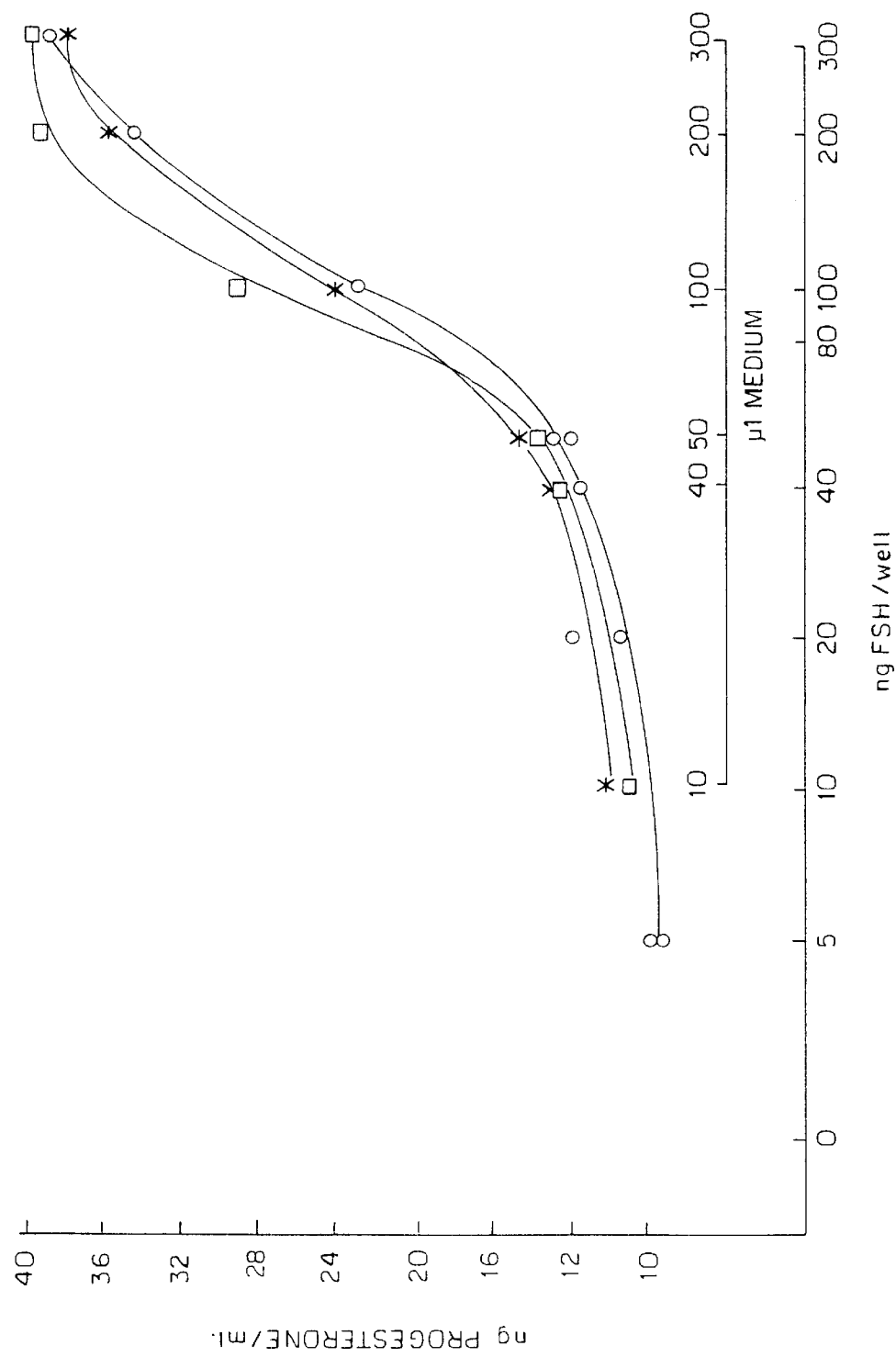
FIG. 31 is a graphical representation of the bioassay of two samples (stars and boxes) of cell supernatants containing recombinant pFSH, and a standard reference control (circles).

The microtiter dishes were placed in a water-saturated incubator at 37° C. in an atmosphere of 95% air and 5% $CO_2$. After 48 hours, supernatants were removed, centrifuged at 100×g for 20 min and samples were taken for determination of progesterone by a highly sensitive and specific radioimmunoassay. The results (FIG. 31) show a dose-dependent increase in the amount-of progesterone found in the medium, which parallels the standard curve for FSH.

EXAMPLE 10

Equine Hormones

COS-7 cells (Gluzman, Cell 23:175, 1981) were split (on the day prior to the transfection) into 100 mm dishes, at $10^6$ cells per dish. 25 ug of equine α DNA (CLSVLP-e α) plus 25 ug of the appropriate equine β subunit DNA (CLSVLP-eFSH or CLSVLP-eLH) were mixed together with 5–10 ug of pJL DNA (which expresses SV40 large-T and has its own SV40 origin of replication, Dunn et al., Cancer cells 3:227, Cold Spring Harbor, 1985) with 0.5 ml of 0.28M NaCl, 0.05M HEPES, and 0.0015M Sodium Phosphate, pH7. 0.5 ml of a mixture of 0.25M $CaCl_2$ and 0.01M HEPES, pH 7.1 was added dropwise, and a precipitate was allowed to form, undisturbed, for 40 minutes.

The precipitate, as a suspension, was added to the cells and allowed to incubate for at least 5 hours at 37° C. in a $CO_2$ incubator. The precipitate and media were removed from the cells and 5 ml of a solution of 15% glycerol in PBS was added to each plate and allowed to incubate for 2 minutes at room temperature. This solution was then removed, the cells were washed twice with 10 ml of PBS, and 5 ml of DMEM+10% fetal bovine serum was added to each plate. Samples were collected after 48 hours incubation and assayed for FSH and LH activities.

Culture medium was collected from the COS cells three days after transfection. Medium was centrifuged at 1000×g for ten minutes to remove particulate matter. Supernatants were concentrated with the Centricon Micro Concentration apparatus purchased from Amicon. Two milliliters of clarified culture medium was added to the sample reservoir. The reservoir was attached to the membrane retentate cup (mw cutoff 24,000 daltons), and the entire apparatus centrifuged at 4000×g for 20 minutes. Solutes with a mw less than 24,000 daltons passed through the membrane while proteins with a mw greater than 24,000 were retained (recovery of proteins with mw greater than 24,000 is typically greater than 95%). All samples were prepared aseptically to allow for analysis by in vitro bioassay as well as radioimmunoassay.

eLH bioactivity was analyzed with the mouse Leydig cell-testosterone production assay (described above). Leydig cells were diluted to $2.5 \times 10^5$ viable cells/ml with Medium 199 containing penicillin (100 U/ml), streptomycin (100 ug/ml) and 0.1% bovine serum albumin. One milliliter of the Leydig cell suspension was added to each 12×75 mm test tube that contained increasing concentrations of a purified LH standard (range from 0–10 ng/tube) or increasing volumes of the concentrated medium samples. All tubes were incubated in a shaking water bath (at 37° C.) for three hours. At the end of this incubation, cells were pelleted by centrifugation and the resulting supernatant was analyzed for testosterone content with a specific testosterone radioimmunoassay. The purified LH preparation stimulated the secretion of testosterone in a dose related fashion to a point where maximal stimulation of the Leydig cells was achieved. eLH bioactivity was present within the concentrated medium range from the equivalent of 1–6 ng/ml of the bovine LH standard.

Concentrated medium samples were prepared as described above from cells transfected with the equine α- and equine FSH β-containing plasmids. Medium samples were analyzed for FSH activity with a dimer-specific bovine FSH radioimmunoassay. This antibody was obtained through the generosity of Dr. James Dias of the Albany Medical College and is directed against the β portion of the FSH dimer. Two of the media samples contained measurable amounts of recombinant equine FSH activity.

The two concentrated medium samples were also assessed for FSH in vitro bioactivity using the granulosa cell-progesterone assay described above. Briefly, granulosa cells were washed several times in Ham F-10 medium containing penicillin, streptomycin and 0.1% bovine serum albumin. Cells were plated at a density of $0.25 \times 10^6$ viable cells/ml/ culture well in Falcon 24-well culture dishes. To each culture was added a dose of a purified FSH standard or increasing volumes of concentrated culture medium. After 3 days incubation, medium samples were collected, centrifuged at 1000×g for 15 minutes to remove debris and analyzed for progesterone content with a specific radioimmunoassay. Increasing doses of FSH cause an increase release of progesterone from the cultured cells into the medium. The concentrated culture samples exhibited FSH activity equivalent to approximately 10–40 ng/ml of the bovine FSH standard employed in the assay.

Having demonstrated how to produce cell lines which express recombinant LH or. FSH, we now demonstrate how production and purification of these recombinant proteins can be achieved on a commercial scale. Once again the following examples are not meant to be limiting to the invention.

EXAMPLE 11
Production of Recombinant Hormones

Recombinant bovine LH was produced in microcarrier spinner cultures from the Cbl 19b cell line. Cell stocks were maintained in 850 cm$^2$ roller bottles with 50 mL of DNA containing 10% fetal bovine serum (FBS) and were routinely screened for bacterial, fungal and mycoplasma contamination.

Both one-liter (culture volume) and eight-liter Bellco glass spinner vessels were used for production runs. Five grams (dry weight) of Cytodex III microcarrier beads were used in the one-liter vessels, while 40 g were used in the eight-liter cultures. The microcarriers were swollen, washed, autoclaved and washed with growth medium following standard procedures specified by the manufacturer. Cultures were initiated by adding freshly trypsinized cells to the prepared microcarriers, to a final concentration of 0.8 to $1.3 \times 10^5$ cell per mL. Three days after inoculation, the medium was changed by allowing the microcarriers to settle, withdrawing 80% of the conditioned medium and adding fresh growth medium. Five days after inoculation, the cells were put into production by removing the spent medium, washing the microcarriers once with one half the culture volume of DME (Delbecco's Modified Eagles medium) and adding the production medium (CEM 2000, Cellular Enhancement Medium, Scott Labs, West Warwick, R.I.). Thereafter, cultures were harvested every two days by allowing the microcarriers to settle, withdrawing 80% of the conditioned medium and adding fresh CEM 2000 (Cellular Enhancement Medium, Scott Laboratory Labs, West Warwick, R.I.). Harvests from day nine onwards were considered to be serum-free and were pooled for purification. Thimerosal was added to all harvested medium at a final concentration of 0.01%, to limit microbial growth.

Yields in one-liter spinners were between 1.3 and 2.0 mg/L per harvest period (48 hours). Approximately 80% of this production occurred on the first day after a medium change. Total production might be increased by changing the medium daily. Production in the eight-liter spinners was from 0.8 to 1.3 mg/L per harvest. These lower levels resulted from lower cell concentrations ($1 \times 10^6$ cells/mL compared with $1.5-2 \times 10^6$ cells/mL in one-liter spinners). Production was continued for 43 days in the one-liter spinners and for 31 and 37 days in the two eight-liter spinners used. A total of 177 mg of crude material in serum-free medium was produced for purification.

Methods employed for the production of recombinant bovine FSH were the same as those described above for LH production. The serum-free growth medium used was CEM+insulin.

Yields in the one-liter spinner cultures were between 1.9 and 5.4 mg/L/harvest. Two one-liter cultures produced 72 mg of crude material for purification, and two more were later set up to produce an additional 109 mg. Cultures were maintained for as long as 38 days.

EXAMPLE 12
Purification of Recombinant Bovine LH

Conditioned media was made to 0.01% Tween 80 and clarified with a 0.5 micron Pall Profile filter cartridge at a, flow rate of 1 l/min. Clarified media was concentrated and flow dialyzed using a Pellican (Millipore) tangential flow cassette with 5 ft.$^2$ of surface area. The membranes were prepared according to manufacturer specifications. Media was concentrated approximately 40 fold and the final buffer composition was 50 mM MES (2-[N-Morpholino] ethanesulfonic acid, pH 6.0), 20 mM NaCl, and 0.01% Tween 80.

The concentrate was loaded on to 2.5×17.5 cm column of Trisacryl M-SP (LKB) which was equilibrated with 50 mM MES, pH6.0, and 20 mM NaCl. The column was washed with two column volumes of this buffer and batch eluted with 0.1M sodium phosphate, pH 9.0, and 0.15 M NaCl. Fractions were assayed by RIA (Radioimmunoassay) and pooled. All procedures were carried out at 4° C.

Reversed phase-HPLC was performed at room temperature using a Waters model 6000A solvent delivery system and model 660 gradient programmer. A Micro-Bondapak phenyl column (Waters, 4.8×300 mm) was equilibrated with 10 mM sodium phosphate pH 7.2 at a flow rate of 1 ml/min. Pooled, S-Sepharose fractions were loaded directly on to the column. After the absorbance at 280 nm returned to baseline, a 30-min. linear gradient from 0 to 70% ethanol in 10 mM phosphate buffer pH 7.2 was applied. One ml fractions were assay by RIA, pooled, and the ethanol removed under vacuum in a Speed Vac Concentrator (Savant).

Pooled fractions were lyophilized and dissolved in about ⅕ volume of 10 mM phosphate, pH 7.2, 0.5M NaCl. HPLC molecular exclusion chromatography was performed with a GF-250 column (DuPont) equilibrated with the same buffer. A maximum of 0.5 ml of sample was loaded. The flow rate was 0.5 ml/min. and the absorbance monitored at 280 nm. Highly purified dimeric hormone was recovered in 2 to 3 0.5 ml fractions at a retention volume of approximately 10 ml.

EXAMPLE 13

Purification of Recombinant Bovine FSH r-bFSH was purified by a three-step procedure employing anion exchange, dye-affinity and hydrophobic interaction chromatography (HIC). The entire process was done at 4° C. with the exception of the HPLC step which was performed at room temperature.

23 L of serum-free, conditioned media was first clarified using a 0.5 μm Pall Profile filter cartridge (P/N: MCY 1001/1005). 0.01% Tween 80 was added to minimize loss by non-specific adsorption. The flow rate was 2.5 L/minutes. There was no loss of activity as measured by RIA.

Clarified media was concentrated and dialyzed with an Amicon spiral tangential flow cartridge (S10Y10) having 10 ft.$^2$ of surface area. The cartridge was prepared and used according to the manufacturer's specifications. The flow rate was 1.5–2 L/min. and the outlet pressure was 25–30 PSI. The media was concentrated approximately 30× then flow dialyzed against 10 mM phosphate buffer, pH 5.0 and 0.01% Tween 80. Dialysis was continued until the conductivity matched that of the starting buffer. This procedure required 6 L of buffer. The final volume of the concentrated and dialyzed pool was approximately 1 L.

Anion exchange chromatography was performed on a 500 ml DEAE Trisacryl LS (LKB) column (9.0×8.0 cm). The column was equilibrated with 10 mM phosphate, pH 6.0, containing 0.01% Tween 80 and flowed at a rate of 42 cm/hr. After loading, the column was washed with three column volumes of buffer then eluted with a 5 L linear gradient from 0 to 0.3M NaCl in 10 mM phosphate. 45 ml fractions were collected, scanned for $A_{280}$ and assayed by RIA.

The pH of the pooled activity was adjusted to 7.5 with 2M NaOH and applied directly onto a 120 ml Blue Trisacryl M (LKB) column at a rate of 37 cm/hour. The column was previously equilibrated in 10 mM phosphate, pH 7.5, 100 mM NaCl and 0.01% Tween 80 and, following the load, washed with three column volumes of the same buffer. The activity was eluted with a 1.2 L linear gradient from 0.1 to 5M NaCl in 10 mM phosphate, pH 7.5, 0.01% Tween. Fractions were again scanned for $A_{280}$ and assayed by RIA.

Pooled activity off the Blue-Trisacryl column, in approximately 2M NaCl, was loaded directly onto a Synchropak Pentyl HPLC column (4.1×250 mm) (SynChrom). The column was equilibrated with 0.8M $(NH_4)_2SO_4$ in 10 mM phosphate buffer, pH 7.0 at a flow rate of 1.0 ml/min. When the $A_{280}$ returned to baseline, a linear, decreasing salt gradient from 0.8 to 0M $(NH_4)_2SO_4$ in 10 mM phosphate, pH 7.0 was applied over 30 minutes. Activity was assayed by RIA, and appropriate fractions collected.

As demonstrated above, the transformed cell lines of the invention are used to produce biologically active heteropolymeric proteins. hCG made according to the invention, for example, has a number of well-known medical uses associated with human fertility. Further, the vectors of the invention which contain enough of one or more of the above cDNA sequences to encode a biologically active or immunologically cross-reactive hormone are useful for production of such hormones, or for production of antibodies to the subunits. By biologically active, we mean that the hormone produced from the heterologous DNA exhibits biological activity in the ungulate of the same type as the naturally occurring hormone. Generally about 80% of the amino acid sequence of the naturally occurring hormone is sufficient. By immunologically cross-reactive, we mean that the hormone undergoes an immunological reaction with monoclonal or polyclonal antibodies that also react with the natural hormone. The immunologically cross-reactive hormones are particularly useful for immunodiagnostics, by well known techniques. For example, antibodies to specific subunits are useful for detecting the presence of a specific hormone; for example, in the urine of a female ungulate to determine the turning of the estrous cycle.

DEPOSITS

The following, described above, have been deposited in the American Type Culture Collection, Rockville, Md.:

α β SVVPl, ATTC VR 2077;

α SVHVPl, ATCC VR 2075;

β SVVPl, ATCC VR 2075;

pRF 375 in C127 cells, ATCC CRL 8401;

pRF 398 in C127 cells, ATCC CRL 8401;

pCL28XhoLHBPV *E. coli*, ATCC CRL 8400;

pRF 398 α $t_2$ in C127 cells ATCC CRL 8400.

Note that αSVHVPl and βSVVPl have been deposited in a mixture of two viruses; and pRF375 and pRF398 have been deposited as a mixture of cells each containing one of the plasmids.

The following vectors have been deposited in the NRRL (Illinois):

pUC18 containing the eα 480 BamHI fragment (IG 5004), NRRL B18127;

pUC18 containing the eLHβ 610 bp PstI fragment (IG 5005), NRRL B18128;

pUC18 containing the e FSHβ 4.4 kb BamHI fragment (IG 5006), NRRL B18139;

pBR322 containing the bov α 730 bp EcoRI fragment (IG 5001), NRRL B18124;

pBR322 containing the bov LHβ 540 bp EcoRI fragment (IG 5002), NRRL B18125;

pBR322 containing the bov FSHβ 540 bp EcoRI BamHI fragment (IG 5003), NRRL B18126;

pBR322 containing the pα 410 bp BamHI fragment (IG 5007), NRRL B18140;

pBR322 pLHB 540 bp (PstI fragment (IG 5008), NRRL B18131; and pBR322 containing the pFSHβ fragment, NRRL B15793.

Deposits B18124, B18126, B18127, B18128 and B18131 were deposited on Oct. 17, 1986; deposits B18139 and B18140 were deposited on Nov. 19, 1986; and deposit B15793 was deposited on Jun. 8, 1984.

Applicants acknowledge their responsibility to replace these cultures should they die before the end of the term of a patent issued hereon, 5 years after the last request for a culture, or 30 years, whichever is the longer, and their responsibility to notify the depository of the issuance of such a patent, at which time the deposits will be made available to the public. Until that time the deposits will be made available to the Commissioner of Patents under the terms of 37 CFR Section 1–14 and 35 USC Section 112.

OTHER EMBODIMENTS

Other embodiments are within the following claims. For example:

Other heteropolymeric proteins, e.g., thyroid stimulating hormone, can be produced, as can human or animal immunoglobulins or immune response antigens.

Other host cells, vectors, promoters, transforming sequences, and viruses can also be employed. The host cell employed generally is dependent on the vector being used. For example, when the vector is replicating virus or non-replicating viral DNA, the host cells are cells capable of being infected or transfected, respectively, by those vectors; e.g., SV40-containing vectors require monkey host cells, preferably CV-1 cells. Where the cloning vector is a plasmid having procaryotic control sequences, prokaryotic host cells, e.g., *E. coli*, are used. Where the cloning vector is a plasmid having eukaryotic control sequences, appropriate eukaryotic host cells, e.g., mouse C127 cells, are used.

What is claimed is:

1. An expression vector encoding two subunits of thyroid stimulating hormone (TSH), each under the control of a separate promoter.

2. The expression vector of claim 1, said expression vector comprising a plasmid.

3. The expression vector of claim 1, said expression vector comprising a replicating virus.

4. A mammalian cell consisting essentially of a cell transfected by a first expression vector, said transfected cell being capable of producing a biologically active heterodimeric thyroid stimulating hormone (TSH) having first and second subunits, each of said subunits of said protein being encoded by said first expression vector under the control of a separate promoter, or progeny of said transfected cell containing the promoters and DNA sequences for said subunits imparted by said vector.

5. The cell of claim 4 wherein, in said transfected, said expression vector is autonomously replicating.

6. The cell of claim 4, wherein said transfected cell is a monkey cell.

7. The cell of claim 4, wherein said transfected cell is a mouse cell.

8. A mammalian cell consisting essentially of a cell transfected by a first expression vector and a distinct second expression vector, said transfected cell being capable of producing a biologically active heterodimeric thyroid stimulating hormone (TSH) having first and second subunits, the first subunit of said protein being encoded by said first expression vector and the second subunit of said protein being encoded by said second expression vector, or progeny of said transfected cell containing the promoters and DNA sequences for said subunits imparted by said vectors.

9. The cell of claim 8 wherein, in said transfected cell, said expression vectors are autonomously replicating.

10. The cell of claim 4 or claim 8, wherein, in said transfected cell, said first vector is a plasmid.

11. The cell of claim 4 or claim 8, wherein, in said transfected cell, transcription of each of the two different subunits of said heterodimer is under the control of an SV40 late promoter.

12. The cell of claim 4 or claim 8, wherein, in said transfected cell, transcription of one subunit of said heterodimer is under the control of the SV40 early promoter, and transcription of the other subunit of said heterodimer is under the control of the mouse metallothionein promoter.

13. The cell of claim 12, wherein, in said transfected cell, said first vector comprises at least the 69% transforming region of the bovine papilloma virus genome.

14. A mammalian cell in accordance with either one of claim 4 or claim 8, wherein said first and second subunits are from the same mammalian species.

15. A mammalian cell consisting essentially of a cell produced by recombinant DNA techniques, said recombinant cell being capable of producing a biologically active thyroid stimulating hormone (TSH), or progeny of said recombinant cell capable of producing said biologically active heterodimeric protein.

16. A method for producing a biologically active heterodimeric protein comprising culturing the mammalian cells of claim 4 or claim 8.

17. A method for producing a biologically active heterodimeric protein comprising culturing the mammalian cells of claim 5 or claim 9.

* * * * *